(12) United States Patent
Moya et al.

(10) Patent No.: US 9,803,165 B2
(45) Date of Patent: Oct. 31, 2017

(54) STIRRED TANK REACTOR AND METHOD

(75) Inventors: Wilson Moya, Concord, MA (US);
Alison Dupont, Sandown, NH (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/610,954

(22) Filed: Sep. 12, 2012

(65) Prior Publication Data

US 2013/0005950 A1    Jan. 3, 2013

Related U.S. Application Data

(62) Division of application No. 12/633,141, filed on Dec. 8, 2009.

(Continued)

(51) Int. Cl.
| | | |
|---|---|---|
| *A23J 1/00* | (2006.01) | |
| *C12M 1/02* | (2006.01) | |
| *C12M 1/00* | (2006.01) | |

(52) U.S. Cl.
CPC ............ *C12M 27/00* (2013.01); *C12M 23/20* (2013.01); *C12M 23/28* (2013.01); *C12M 47/12* (2013.01)

(58) Field of Classification Search
None
See application file for complete search history.

(56) References Cited

U.S. PATENT DOCUMENTS

| | | |
|---|---|---|
| 2,923,669 A | 2/1960 | Poitras |
| 3,211,645 A | 10/1965 | Ferrari |

(Continued)

FOREIGN PATENT DOCUMENTS

| | | | |
|---|---|---|---|
| EP | 0162034 | * 11/1990 | ............. C12P 21/00 |
| EP | 0162034 B1 | 11/1990 | |

(Continued)

OTHER PUBLICATIONS

Agarwal (1996) Prot Exp and Pur 7: 294-298.*

(Continued)

*Primary Examiner* — Melanie Y Brown
*Assistant Examiner* — Richard Moerschell
(74) *Attorney, Agent, or Firm* — Nields, Lemack & Frame, LLC

(57) ABSTRACT

Container for sample preparation or processing, such as biomass culturing or processing, and optionally sample purification. In certain embodiments, the reactor is a bioreactor that includes a stirred cell device that simulates a tangential flow filter to reduce or eliminate clogging that can be caused by the solids generated. In certain embodiments, the solids comprise a precipitate or floc or beads, such as one that includes a polymer that binds the biomolecule(s) of interest, and impurities. In its method aspects, embodiments disclosed herein include purification and isolation of biomolecules of interest derived from cell culture fluids. The methods include carrying out sample preparation or processing in a container, culturing a biomass; generating solids by precipitating or flocculating a biomolecule of interest from the cultured broth; preventing the solids from settling in the container by agitation; and purification, such as by eluting the biomolecule of interest and filtering the same.

1 Claim, 7 Drawing Sheets

Related U.S. Application Data

(60) Provisional application No. 61/201,865, filed on Dec. 16, 2008.

(56) References Cited

U.S. PATENT DOCUMENTS

| | | | |
|---|---|---|---|
| 3,556,302 A | 1/1971 | Agranant |
| 3,565,973 A | 2/1971 | Michaels |
| 3,632,507 A | 1/1972 | Witt |
| 3,702,806 A | 11/1972 | Oliva |
| 3,737,377 A | 6/1973 | Sternberg |
| 3,859,212 A | 1/1975 | Smalley et al. |
| 3,968,037 A | 7/1976 | Morgan et al. |
| 4,045,377 A | 8/1977 | Pearson |
| 4,055,469 A | 10/1977 | Snoke et al. |
| 4,200,695 A | 4/1980 | Chong et al. |
| 4,215,198 A | 7/1980 | Gordon |
| 4,305,829 A | 12/1981 | Kelsey et al. |
| 4,317,726 A | 3/1982 | Shepel |
| 4,359,537 A | 11/1982 | Chong |
| 4,371,674 A | 2/1983 | Hertel et al. |
| 4,380,590 A | 4/1983 | Chong |
| 4,382,028 A | 5/1983 | Paget |
| 4,450,078 A | 5/1984 | Walker et al. |
| 4,515,893 A | 5/1985 | Kung et al. |
| 4,528,933 A | 7/1985 | Allen |
| 4,536,294 A | 8/1985 | Guillet et al. |
| 4,676,980 A | 6/1987 | Segal et al. |
| 4,780,409 A | 10/1988 | Monji et al. |
| 4,816,567 A | 3/1989 | Cabilly et al. |
| 4,828,701 A | 5/1989 | Cussler |
| 4,839,046 A | 6/1989 | Chandler |
| 4,863,613 A | 9/1989 | Johnson et al. |
| 4,904,385 A | 2/1990 | Wessling et al. |
| 4,912,032 A | 3/1990 | Hoffman et al. |
| 4,925,785 A | 5/1990 | Wang et al. |
| 4,968,435 A | 11/1990 | Neff et al. |
| 5,003,047 A | 3/1991 | Yarmush et al. |
| 5,047,511 A | 9/1991 | Mehrotra |
| 5,091,178 A | 2/1992 | Hellstrom et al. |
| 5,091,313 A | 2/1992 | Chang |
| 5,116,754 A | 5/1992 | Fraser et al. |
| 5,139,031 A | 8/1992 | Guirguis |
| 5,152,903 A | 10/1992 | Neff et al. |
| 5,164,057 A | 11/1992 | Mori et al. |
| 5,171,450 A | 12/1992 | Hoots |
| 5,208,161 A | 5/1993 | Saunders et al. |
| 5,238,545 A | 8/1993 | Yoshioka et al. |
| 5,258,122 A | 11/1993 | Ha et al. |
| 5,324,787 A | 6/1994 | Pinschmidt, Jr. et al. |
| 5,340,865 A | 8/1994 | Neff et al. |
| 5,342,581 A | 8/1994 | Sanadi |
| 5,354,481 A | 10/1994 | Neff et al. |
| 5,354,801 A | 10/1994 | O'Toole |
| 5,374,971 A | 12/1994 | Clapp et al. |
| 5,430,110 A | 7/1995 | Ahlers et al. |
| 5,512,480 A | 4/1996 | Sandstrom et al. |
| 5,525,519 A | 6/1996 | Woiszwillo |
| 5,573,675 A | 11/1996 | Sommese et al. |
| 5,599,719 A | 2/1997 | Woiszwillo et al. |
| 5,622,700 A | 4/1997 | Jardieu et al. |
| 5,622,857 A | 4/1997 | Goffe |
| 5,672,347 A | 9/1997 | Aggarwal et al. |
| 5,684,107 A | 11/1997 | Schneider et al. |
| 5,693,762 A | 12/1997 | Queen et al. |
| 5,714,338 A | 2/1998 | Wai Fei et al. |
| 5,721,108 A | 2/1998 | Robinson et al. |
| 5,725,856 A | 3/1998 | Hudziak et al. |
| 5,728,559 A | 3/1998 | Nilsson et al. |
| 5,733,507 A | 3/1998 | Zakim |
| 5,736,137 A | 4/1998 | Anderson et al. |
| 5,739,383 A | 4/1998 | Yoon et al. |
| 5,770,358 A | 6/1998 | Dower et al. |
| 5,807,489 A | 9/1998 | Farinato et al. |
| 5,840,804 A | 11/1998 | Carl et al. |
| 5,840,851 A | 11/1998 | Plomer et al. |
| 5,846,816 A * | 12/1998 | Forth ........................ 435/292.1 |
| 5,879,564 A | 3/1999 | Farinato |
| 5,929,214 A | 7/1999 | Peters et al. |
| 5,962,649 A | 10/1999 | Noda et al. |
| 5,994,560 A | 11/1999 | Yoon et al. |
| 5,998,588 A | 12/1999 | Hoffman et al. |
| 6,024,955 A | 2/2000 | Asano et al. |
| 6,121,428 A | 9/2000 | Blank et al. |
| 6,127,526 A | 10/2000 | Blank |
| 6,133,047 A | 10/2000 | Elaissari et al. |
| 6,139,746 A | 10/2000 | Kopf |
| 6,147,176 A | 11/2000 | Neff et al. |
| 6,153,104 A | 11/2000 | Robertson |
| 6,191,242 B1 | 2/2001 | Ryles et al. |
| 6,197,522 B1 | 3/2001 | Keller et al. |
| 6,221,655 B1 * | 4/2001 | Fung et al. ................ 435/288.1 |
| 6,245,555 B1 | 6/2001 | Curtis |
| 6,258,275 B1 | 7/2001 | Freitag et al. |
| 6,294,622 B1 | 9/2001 | Barajas et al. |
| 6,300,142 B1 | 10/2001 | Andrewes et al. |
| 6,307,013 B1 | 10/2001 | Chivers |
| 6,358,730 B1 | 3/2002 | Kane |
| 6,367,749 B2 | 4/2002 | Valiulis |
| 6,372,141 B1 | 4/2002 | Okano et al. |
| 6,374,684 B1 | 4/2002 | Dority |
| 6,420,487 B1 | 7/2002 | Vaidya et al. |
| 6,454,950 B1 | 9/2002 | Tjerneld et al. |
| 6,521,341 B1 | 2/2003 | Elaissari et al. |
| 6,534,633 B1 | 3/2003 | Weidanz et al. |
| 6,538,089 B1 | 3/2003 | Samra et al. |
| 6,544,424 B1 | 4/2003 | Shevitz |
| 6,565,872 B2 | 5/2003 | Wu et al. |
| 6,582,926 B1 | 6/2003 | Chilkoti |
| 6,605,714 B2 | 8/2003 | Vaidya et al. |
| 6,638,918 B2 | 10/2003 | Davison et al. |
| 6,641,735 B1 | 11/2003 | Yoshizako et al. |
| 6,673,598 B1 | 1/2004 | Akers et al. |
| 6,676,840 B2 | 1/2004 | Tarbet et al. |
| 6,689,836 B2 | 2/2004 | Vaidya et al. |
| 6,706,187 B1 | 3/2004 | Okano et al. |
| 6,709,862 B2 | 3/2004 | Curtis |
| 6,716,593 B1 * | 4/2004 | Robins et al. ................ 435/7.92 |
| 6,737,235 B1 | 5/2004 | Cros et al. |
| 6,765,081 B2 | 7/2004 | Lin et al. |
| 6,770,758 B2 | 8/2004 | Pan et al. |
| 6,805,793 B2 | 10/2004 | Yoshizako et al. |
| 6,821,515 B1 | 11/2004 | Cleland et al. |
| 6,830,670 B1 | 12/2004 | Viovy et al. |
| 6,852,819 B2 | 2/2005 | Ohnishi et al. |
| 6,858,694 B2 | 2/2005 | Ohnishi et al. |
| 6,863,437 B2 | 3/2005 | Ohnishi et al. |
| 6,867,268 B2 | 3/2005 | Vaidya et al. |
| 6,926,832 B2 | 8/2005 | Collins et al. |
| 6,956,077 B1 | 10/2005 | Akiyama et al. |
| 6,967,085 B1 | 11/2005 | Hughes et al. |
| 6,974,660 B2 | 12/2005 | Manias et al. |
| 7,001,953 B2 | 2/2006 | Chen et al. |
| 7,011,930 B2 | 3/2006 | Manias et al. |
| 7,012,136 B2 | 3/2006 | Yamanaka et al. |
| 7,052,917 B1 | 5/2006 | Ohnishi et al. |
| 7,070,696 B2 | 7/2006 | Weir et al. |
| 7,083,948 B1 | 8/2006 | Sassenfeld et al. |
| 7,157,603 B2 | 1/2007 | Hilbrig |
| 7,160,971 B2 | 1/2007 | Mallapragada et al. |
| 7,169,908 B2 | 1/2007 | Lester et al. |
| 7,195,925 B2 | 3/2007 | Ohnishi et al. |
| 7,300,545 B2 | 11/2007 | Ohara et al. |
| 7,355,020 B2 | 4/2008 | Yamanaka et al. |
| 7,364,859 B2 | 4/2008 | Chilkoti |
| 7,377,686 B2 | 5/2008 | Hubbard |
| 7,393,698 B2 | 7/2008 | Furukawa et al. |
| 7,422,724 B1 | 9/2008 | Manginell et al. |
| 7,429,458 B2 | 9/2008 | Chilkoti |
| 7,442,515 B2 | 10/2008 | Ratner et al. |
| 7,514,007 B2 | 4/2009 | Chen et al. |
| 7,541,167 B2 | 6/2009 | Dave et al. |
| 7,547,747 B2 | 6/2009 | Hashimoto et al. |
| 7,553,658 B2 | 6/2009 | Kepka et al. |
| 7,556,835 B2 | 7/2009 | Hultin et al. |

(56) References Cited

U.S. PATENT DOCUMENTS

| | | |
|---|---|---|
| 7,625,764 B2 | 12/2009 | Stayton et al. |
| 7,632,656 B2 | 12/2009 | Kanazawa et al. |
| 7,695,905 B2 | 4/2010 | Furukawa et al. |
| 7,718,193 B2 | 5/2010 | Stayton et al. |
| 7,767,399 B2 | 8/2010 | Murphy et al. |
| 7,981,688 B2 | 7/2011 | Stayton et al. |
| 8,093,026 B2 | 1/2012 | Elaissari et al. |
| 8,110,351 B2 | 2/2012 | Bosnes |
| 8,133,457 B2 | 3/2012 | Ribault et al. |
| 8,137,559 B2 | 3/2012 | Katzke et al. |
| 8,163,886 B2* | 4/2012 | Moya ............... 530/390.1 |
| 8,241,591 B2 | 8/2012 | Ribault et al. |
| 8,263,343 B2 | 9/2012 | Hallgren et al. |
| 8,313,902 B2 | 11/2012 | Furukawa et al. |
| 8,362,217 B2* | 1/2013 | Moya ............... 530/390.5 |
| 8,499,576 B2 | 8/2013 | Meijer |
| 8,507,283 B2 | 8/2013 | Stayton et al. |
| 8,569,464 B2 | 10/2013 | Moya et al. |
| 8,691,918 B2 | 4/2014 | Jaber et al. |
| 8,877,477 B2 | 11/2014 | Woonton et al. |
| 8,915,374 B2 | 12/2014 | Franks et al. |
| 8,999,702 B2 | 4/2015 | Kelly, Jr. et al. |
| 9,080,933 B2 | 7/2015 | Stayton et al. |
| 9,090,930 B2 | 7/2015 | Ribault et al. |
| 9,174,860 B2 | 11/2015 | Franks et al. |
| 9,217,048 B2 | 12/2015 | Jaber et al. |
| 9,376,464 B2 | 6/2016 | Moya et al. |
| 9,410,181 B2 | 8/2016 | Ribault et al. |
| 2001/0018513 A1 | 8/2001 | Baker |
| 2002/0058786 A1 | 5/2002 | Chivers |
| 2002/0098567 A1 | 7/2002 | Vaidya et al. |
| 2003/0059840 A1 | 3/2003 | Chilkoti |
| 2003/0085228 A1 | 5/2003 | Oakes |
| 2003/0186293 A1 | 10/2003 | Ohnishi et al. |
| 2004/0009473 A1 | 1/2004 | Pease |
| 2004/0010163 A1 | 1/2004 | Hilbrig |
| 2004/0029143 A1 | 2/2004 | Van Ness et al. |
| 2004/0039177 A1 | 2/2004 | Yamanaka et al. |
| 2004/0058436 A1 | 3/2004 | Zhang et al. |
| 2004/0062140 A1 | 4/2004 | Cadogan et al. |
| 2004/0134846 A1 | 7/2004 | Akiyama et al. |
| 2004/0185437 A1 | 9/2004 | Hermet et al. |
| 2004/0219628 A1 | 11/2004 | Tashiro et al. |
| 2004/0248774 A1 | 12/2004 | Tayot |
| 2005/0016620 A1 | 1/2005 | Proulx et al. |
| 2005/0063259 A1 | 3/2005 | Isshiki et al. |
| 2005/0158782 A1 | 7/2005 | Furukawa et al. |
| 2005/0158851 A1 | 7/2005 | Furey et al. |
| 2005/0175702 A1 | 8/2005 | Muller-Schulte |
| 2005/0224415 A1 | 10/2005 | Akiyama et al. |
| 2005/0238620 A1* | 10/2005 | Gomer et al. ............... 424/85.2 |
| 2005/0272146 A1 | 12/2005 | Hodge et al. |
| 2005/0282169 A1 | 12/2005 | Turner et al. |
| 2006/0118471 A1 | 6/2006 | Vidalinc |
| 2006/0121519 A1 | 6/2006 | Patchornik |
| 2006/0162882 A1 | 7/2006 | O'Hara et al. |
| 2006/0189795 A1 | 8/2006 | Van Alstine et al. |
| 2006/0251610 A1 | 11/2006 | Nakahama |
| 2006/0257993 A1 | 11/2006 | McDevitt et al. |
| 2006/0270036 A1* | 11/2006 | Goodwin et al. ............. 435/395 |
| 2006/0281158 A1 | 12/2006 | Felder et al. |
| 2007/0148437 A1 | 6/2007 | Muller-Schulte |
| 2007/0193954 A1 | 8/2007 | Busson |
| 2007/0224241 A1 | 9/2007 | Stayton et al. |
| 2007/0249737 A1 | 10/2007 | Miller et al. |
| 2007/0298451 A1 | 12/2007 | Ribault et al. |
| 2008/0032396 A1 | 2/2008 | Chokshi |
| 2008/0131957 A1 | 6/2008 | Ryan et al. |
| 2008/0160559 A1 | 7/2008 | Carre et al. |
| 2008/0193981 A1 | 8/2008 | Fahrner et al. |
| 2008/0220531 A1 | 9/2008 | Stayton et al. |
| 2008/0254500 A1 | 10/2008 | Tashiro et al. |
| 2008/0255027 A1 | 10/2008 | Moya et al. |
| 2008/0284163 A1 | 11/2008 | Proulx et al. |
| 2008/0293118 A1 | 11/2008 | Furukawa et al. |
| 2008/0293926 A1 | 11/2008 | Hallgren et al. |
| 2009/0001025 A1 | 1/2009 | Takahashi et al. |
| 2009/0036651 A1 | 2/2009 | Moya |
| 2009/0050566 A1 | 2/2009 | Kozlov et al. |
| 2009/0130704 A1 | 5/2009 | Gyure |
| 2009/0148961 A1 | 6/2009 | Luchini et al. |
| 2009/0155201 A1 | 6/2009 | Mandeville, III et al. |
| 2009/0181450 A1 | 7/2009 | Ribault et al. |
| 2009/0182120 A1 | 7/2009 | Utermohlen et al. |
| 2009/0232737 A1* | 9/2009 | Moya et al. ............... 424/9.1 |
| 2009/0233327 A1 | 9/2009 | Lau et al. |
| 2009/0311776 A1 | 12/2009 | Kelly, Jr. et al. |
| 2010/0012589 A1 | 1/2010 | Ribault et al. |
| 2010/0190963 A1 | 7/2010 | Moya et al. |
| 2010/0193148 A1 | 8/2010 | McKay et al. |
| 2010/0200507 A1 | 8/2010 | Kozlov et al. |
| 2010/0209987 A1 | 8/2010 | Elaissari et al. |
| 2010/0215749 A1 | 8/2010 | Stayton et al. |
| 2010/0267933 A1* | 10/2010 | Wilson ............... 530/387.3 |
| 2010/0282425 A1 | 11/2010 | Karppi et al. |
| 2011/0020327 A1 | 1/2011 | Moya et al. |
| 2011/0045081 A1 | 2/2011 | Steitz et al. |
| 2011/0065900 A1 | 3/2011 | Johansson et al. |
| 2011/0174735 A1 | 7/2011 | Ribault et al. |
| 2011/0257435 A1 | 10/2011 | Favero et al. |
| 2011/0313066 A1 | 12/2011 | Jaber et al. |
| 2012/0070836 A1 | 3/2012 | Zillmann et al. |
| 2012/0077249 A1 | 3/2012 | Ramaswamy et al. |
| 2012/0283419 A1 | 11/2012 | Thiyagarajan et al. |
| 2013/0123476 A1 | 5/2013 | Moya |
| 2013/0137860 A1 | 5/2013 | Moya et al. |
| 2013/0317204 A1 | 11/2013 | Moya et al. |
| 2014/0171594 A1 | 6/2014 | Jaber et al. |
| 2014/0263011 A1 | 9/2014 | Thiyagarajan et al. |
| 2015/0018440 A1 | 1/2015 | Woonton et al. |
| 2015/0133636 A1 | 5/2015 | Xenopoulos et al. |
| 2015/0218208 A1 | 8/2015 | Koguma et al. |
| 2015/0239956 A1 | 8/2015 | Koguma et al. |
| 2015/0268236 A1 | 9/2015 | Stayton et al. |
| 2015/0291656 A1 | 10/2015 | Hobel et al. |

FOREIGN PATENT DOCUMENTS

| | | |
|---|---|---|
| EP | 0534016 A1 | 3/1993 |
| EP | 0420937 B1 | 11/1994 |
| EP | 0922715 A2 | 6/1999 |
| EP | 0851768 B1 | 4/2002 |
| EP | 1312643 B1 | 5/2005 |
| EP | 1532243 B1 | 5/2005 |
| EP | 1201667 B1 | 9/2005 |
| EP | 1832341 A1 | 9/2007 |
| EP | 1923461 A1 | 5/2008 |
| EP | 1312671 B1 | 4/2009 |
| EP | 1969292 B1 | 3/2011 |
| EP | 2344517 B1 | 6/2014 |
| EP | 1928580 B1 | 8/2014 |
| GB | 2297926 A | 8/1996 |
| GB | 2305936 A | 4/1997 |
| JP | 5-95778 A | 4/1993 |
| JP | 6-38732 A | 2/1994 |
| JP | 6-116169 A | 4/1994 |
| JP | 6-141890 A | 5/1994 |
| JP | 9-12598 A | 1/1997 |
| JP | 11-505714 A | 5/1999 |
| JP | 2000-500733 A | 1/2000 |
| JP | 2000-86729 A | 3/2000 |
| JP | 2000-507927 A | 6/2000 |
| JP | 2001-517632 A | 10/2001 |
| JP | 2002-538430 A | 11/2002 |
| JP | 2003-114175 A | 4/2003 |
| JP | 2003-153684 A | 5/2003 |
| JP | 2006-284604 A | 10/2006 |
| JP | 2007-32559 A | 2/2007 |
| JP | 2008-519277 A | 6/2008 |
| JP | 5612761 B2 | 10/2014 |
| KR | 10-2009-0113264 A | 10/2009 |
| KR | 10-1551295 B1 | 9/2015 |
| WO | 91/00360 A1 | 1/1991 |
| WO | 92/00373 A1 | 1/1992 |

(56) References Cited

FOREIGN PATENT DOCUMENTS

| | | |
|---|---|---|
| WO | 92/20373 A1 | 11/1992 |
| WO | 93/04173 A1 | 3/1993 |
| WO | 93/08829 A1 | 5/1993 |
| WO | 93/14110 A1 | 7/1993 |
| WO | 93/16185 A2 | 8/1993 |
| WO | 94/15951 A1 | 7/1994 |
| WO | 95/06249 A1 | 3/1995 |
| WO | 95/19181 A1 | 7/1995 |
| WO | 95/23865 A1 | 9/1995 |
| WO | 96/02577 A1 | 2/1996 |
| WO | 96/27011 A1 | 9/1996 |
| WO | 96/30046 A1 | 10/1996 |
| WO | 96/37600 A1 | 11/1996 |
| WO | 96/40210 A1 | 12/1996 |
| WO | 97/26912 A2 | 7/1997 |
| WO | 98/06248 A2 | 2/1998 |
| WO | 98/23761 A1 | 6/1998 |
| WO | 98/33162 A1 | 7/1998 |
| WO | 98/45331 A2 | 10/1998 |
| WO | 98/51793 A1 | 11/1998 |
| WO | 99/01556 A2 | 1/1999 |
| WO | 99/15186 A1 | 4/1999 |
| WO | 99/35500 A1 | 7/1999 |
| WO | 00/12618 A1 | 3/2000 |
| WO | 00/46262 A1 | 8/2000 |
| WO | 00/67901 A1 | 11/2000 |
| WO | 00/75348 A1 | 12/2000 |
| WO | 01/07548 A1 | 2/2001 |
| WO | 01/40309 A2 | 6/2001 |
| WO | 01/52612 A2 | 7/2001 |
| WO | 03/101486 A2 | 12/2003 |
| WO | 2004/056312 A2 | 7/2004 |
| WO | 2004/092393 A1 | 10/2004 |
| WO | 2005/010141 A2 | 2/2005 |
| WO | 2005/021129 A1 | 3/2005 |
| WO | 2005/108546 A2 | 11/2005 |
| WO | 2005/118771 A2 | 12/2005 |
| WO | 2006/085321 A2 | 8/2006 |
| WO | 2006/138143 A1 | 12/2006 |
| WO | 2007/002690 A2 | 1/2007 |
| WO | 2007/038523 A2 | 4/2007 |
| WO | 2007/073311 A1 | 6/2007 |
| WO | 2007/104456 A1 | 9/2007 |
| WO | 2007/148230 A2 | 12/2007 |
| WO | 2008/004988 A1 | 1/2008 |
| WO | 2008/079280 A1 | 7/2008 |
| WO | 2008/079302 A2 | 7/2008 |
| WO | 2008/091740 A2 | 7/2008 |
| WO | 2008/097154 A1 | 8/2008 |
| WO | 2008/109667 A2 | 9/2008 |
| WO | 2009/089570 A1 | 7/2009 |
| WO | 2009/141664 A1 | 11/2009 |
| WO | 2009/158606 A2 | 12/2009 |
| WO | 2010/082894 A1 | 7/2010 |
| WO | 2014/090838 A1 | 6/2014 |
| WO | 2014/123484 A1 | 8/2014 |
| WO | 2014/123485 A1 | 8/2014 |
| WO | 2014/133458 A1 | 9/2014 |
| WO | 2014/133459 A1 | 9/2014 |
| WO | 2014/133460 A1 | 9/2014 |

OTHER PUBLICATIONS

Office Action mailed Jan. 31, 2013 in corresponding U.S. Appl. No. 12/633,141.
Office Action mailed Mar. 15, 2013 in co-pending U.S. Appl. No. 13/108,576.
Final Rejection mailed Jun. 25, 2013 in corresponding U.S. Appl. No. 12/633,141.
International Preliminary Report on Patentability mailed Jun. 30, 2011 in co-pending PCT application No. PCT/US2009/006363.
International Preliminary Report on Patentability mailed Nov. 29, 2012 in co-pending PCT application No. PCT/US2011/036648.
International Preliminary Report on Patentability mailed Dec. 20, 2012 in co-pending PCT application No. PCT/US2011/039595.
Merriam Webster Dictionary, accessed May 14, 2013 at http://www.merriam-webster.com/dictionary/associated, Definition of the word "associate . . . " 6 pages.
Restriction mailed May 9, 2013 in co-pending U.S. Appl. No. 13/747,495.
Office Action mailed Apr. 30, 2013 in co-pending U.S. Appl. No. 13/155,912.
Office Action mailed Apr. 15, 2013 in co-pending U.S. Appl. No. 13/108,576.
Notice of Allowance mailed Aug. 21, 2013 in co-pending U.S. Appl. No. 12/316,708.
Final Rejection mailed Aug. 19, 2013 in co-pending U.S. Appl. No. 12/387,688.
Biotechnol. Appl. Biochem. (1999), vol. 30, pp. 235-244, "Expression system for foreign genes using the fission yeast *Schizosaccharomyces pombe*", Giga-Hama, et al.
European Search Report mailed Jul. 9, 2013 in corresponding European Patent Application No. EP 09835506.8.
Office Action mailed Nov. 25, 2013 in co-pending U.S. Appl. No. 13/747,495.
Office Action mailed Dec. 9, 2013 in co-pending U.S. Appl. No. 13/955,024.
Notice of Allowance mailed Nov. 22, 2013 in co-pending U.S. Appl. No. 13/108,576.
Office Action—Restriction—mailed Oct. 28, 2013 in co-pending U.S. Appl. No. 13/955,024.
Final Rejection mailed Oct. 22, 2013 in co-pending U.S. Appl. No. 13/108,576.
Protein Expression and Purification, vol. 7, Article No. 0042, 1996, pp. 294-298, "Sequential Precipitation with Reversibly Soluble Insoluble Polymers as a Bioseparation Strategy: Purification of B-Glucosidase from *Trichoderma longibrachiatum*", Agarwal, et al.
Journal of Chromatography B, vol. 761, No. 2, 2001, pp. 247-254, "New antibody purification procedure using a thermally responsive poly(N-isopropylacrylamide)-dextran derivative conjugate", Anastase-Ravion, et al.
Cell, vol. 61, No. 7, Jun. 1990, pp. 1303-1313, "CD44 is the Principal Cell Surface Receptor for Hyaluronate", Aruffo, et al.
Process Technology Proceedings, vol. 4, Proceedings of the International Symposium on Flocculation in Biotechnology and Separations Systems, San Francisco, California, Jul. 28-Aug. 1, 1986, pp. 429 & 441, "Flocculation in Biotechnology and Separation Systems", Attia.
Journal of Chromatography A, vol. 1119, 2006, pp. 58-65, "Aqueous chromatography system using pH- and temperature-responsive stationary phase with ion-exchange groups", Ayano, et al.
Science, vol. 229, Jul. 1985, pp. 81-83, "Preparation of Bispecific Antibodies by Chemical Recombination of Monoclonal Immunoglobulin G1 Fragments", Brennan, et al.
Monoclonal Antibody Production Techniques and Application, pp. 51-63 (Marcel Dekker, Inc., New York 1987), "Mouse-Human Myeloma Partners for the Production of Heterohybridomas", Brodeur, et al.
The Year in Immunology, vol. 7, 1993, pp. 33-40, "Designer Mice: The Production of Human Antibody Repertoires in Transgenic Animals", Bruggemann, et al.
Bio/Technology, Nature Publishing Group, vol. 10, Feb. 1992, pp. 163-167, "High Level *Escherichia coli* Expression and Production of a Bivalent Humanized Antibody Fragment", Carter, et al.
Macromolecular Bioscience, vol. 5, No. 5, 2005, pp. 373-378, "Highly Branched Stimuli Responsive Poly[(N-isopropylacrylamide)-co-(1,2-propandiol-3-methacrylate)]s with Protein Binding Functionality", Carter, et al.
Proc. Natl. Acad. Sci. USA, vol. 89, May 1992, pp. 4285-4289, "Humanization of an anti-p185HER2 antibody for human cancer therapy", Carter, et al.
"Technology: Temperature-responsive polymers", document retrieved on Oct. 13, 2010, available at: http://www.cellseed.com/technology-e/index.html, 1 page, Cellseed, Inc.

(56) References Cited

OTHER PUBLICATIONS

Cancer Research (Suppl.), vol. 55, Dec. 1, 1995, pp. 5852s-5856s, "Biological Activity of Two Humanized Antibodies against Two Different Breast Cancer Antigens and Comparison to Their Original Murine Forms", Ceriani, et al.
Macromolecular Chemistry and Physics, vol. 196, No. 4, Apr. 1995, pp. 1251-1259, "A new temperature- and pH-responsive copolymer for possible use in protein conjugation", Chen, et al.
Nature, vol. 373, No. 5, Jan. 1995, pp. 49-52, "Graft copolymers that exhibit temperature-induced phase transitions over a wide range of pH", Chen, et al.
Langmuir, vol. 21, No. 25, 2005, pp. 11673-11677, "pH-Dependence of the Properties of Hydrophobically Modified Polyvinylamine", Chen, et al.
Biomaterials, vol. 11, No. 9, Nov. 1990, pp. 631-633, "Polymer-protein conjugates. II. Affinity precipitation separation of human immunogammaglobulin by a poly (N-isopropylacrylamide)-protein A conjugate", Chen, et al.
Colloids and Surfaces B: Biointerfaces, vol. 6, 1996, pp. 37-49, "Characterization of pH-sensitive polymeric supports for selective precipitation of proteins", Chern, et al.
Journal of Molecular Biology, vol. 196, 1987, pp. 901-917, "Canonical Structures for the Hypervariable Regions of Immunoglobulins", Chothia, et al.
Arthritis & Rheumatism, vol. 39, No. 1, Jan. 1996, pp. 52-56, "Percentage of anti-CD4 monoclonal antibody-coated lymphocytes in the rheumatoid joint is associated with clinical improvement. Implications for the development of immunotherapeutic dosing regimens", Choy, et al.
Nature, vol. 352, Aug. 1991, pp. 624-628, "Making antibody fragments using phage display libraries", Clackson, et al.
Bioseparation, vol. 7, No. 4-5, Jul. 1999, pp. 231-240, "Affinity precipitation of monoclonal antibodies by nonstoichiometric polyelelectrolyte complexes", Dainiak, et al.
Journal of Colloid and Interface Science, vol. 179, No. 1, 1996, pp. 188-193, "Temperature-Sensitive Flocculants Based on Poly (N-isopropylacrylamide-co-diallyldimethylammonium Chloride)", Deng, et al.
Critical Care Medicine, vol. 23, No. 9, Sep. 1995, pp. 1461-1469, "CDP571, a humanized antibody to human tumor necrosis factor-alpha: Safety, pharmacokinetics, immune response, and influence of the antibody on cytokine concentrations in patients with septic shock", Dhainaut, et al.
Nature, vol. 411, May 2001, pp. 59-62, "Size-dependent control of the binding of biotinylated proteins to streptavidin using a polymer shield", Ding, et al.
Nature, vol. 355, Jan. 1992, pp. 258-262, "Immunization of hu-PBL-SCID mice and the rescue of human monoclonal Fab fragments through combinatorial libraries", Duchosal, et al.
Journal of Polymer Science, vol. XIII, No. 6, Feb. 1954, pp. 85-91, "Viscosities of Dilute Aqueous Solutions of a Partially Quaternized Poly-4-vinylpyridine at Low Gradients of Flow", Eisenberg, et al.
The Journal of Immunology, vol. 155, No. 2, 1995, pp. 925-937, "Engineered Anti-CD38 Monoclonal Antibodies for Immunotherapy of Multiple Myeloma", Ellis, et al.
Flocculation in Biotechnology and Separation Systems, 1987, pp. 441-455, "Flocculation of *E. coli* Bacteria With Cationic Polyelectrolytes", Eriksson, et al.
Flocculation in Biotechnology and Separation Systems, 1987, pp. 383-398, "Genetic Control of Flocculation of Yeast With Respect to Application in Biotechnology", Esser, et al.
Journal of Chromatography A, vol. 1195, 2008, pp. 94-100, "Purification of human immunoglobulin G by thermoseparating aqueous two-phase systems", Ferriera, et al.
Biotechnology and Bioengineering, vol. 79, No. 3, Aug. 5, 2002, pp. 271-276, "Affinity Separation Using an Fv Antibody Fragment-"Smart" Polymer Conjugate", Fong, et al.
Bioconjugate Chem., vol. 10, No. 5, 1999, pp. 720-725, "Thermoprecipitation of Steptavidin via Oligonucleotide-Mediated Self-Assembly with Poly (N-isopropylacrylamide)", Fong, et al.

Chimia 55, No. 3, 2001, pp. 196-200, "Stimulus-Responsive Polymers for Bioseparation", Freitag, et al.
Trends in Biotechnology, vol. 9, No. 6, Jun. 1991, pp. 191-196, "Application of reversibly soluble polymers in bioprocessing", Fujii, et al.
Trends in Biotechnology, vol. 17, No. 8, Aug. 1999, pp. 335-340, "'Smart' polymers and what they could do in biotechnology and medicine", Galaev, et al.
Russian Chemical Reviews, vol. 64, No. 5, 1995, pp. 471-489, "'Smart' polymers in biotechnology and medicine", Galaev.
Journal of Chromatography A, vol. 684, 1994, pp. 45-54, "Interaction of Cibacron Blue with polymers: implications for polymer-shielded dye-affinity chromatography of phosphofructokinase from baker's yeast", Galaev, et al.
Biotechnology and Bioengineering, vol. 71, No. 3, 2000/2001, pp. 223-234, "Use of the Avidin (Imino)biotin System as a General Approach to Affinity Precipitation", Garret-Flaudy, et al.
Process Biochemistry, vol. 34, No. 6-7, Sep. 1999, pp. 577-580, "Purification of *Aspergillus* sp xylanase by precipitation with an anionic polymer Eudragit S 100", Gawande, et al.
Progress in Polymer Science, vol. 29, No. 12, Dec. 2004, pp. 1173-1222, "Stimuli-responsive polymers and their bioconjugates", Gil, et al.
Monoclonal Antibodies: Principles and Practice, Academic Press, 1986, pp. 59-103, "3. Production of Monoclonal Antibodies", Goding.
The Journal of Immunology, vol. 155, No. 10, 1995, pp. 4996-5002, "Construction and Characterization of a Humanized Anti-gamma-Ig Receptor Type I (Fc gamma RI) Monoclonal Antibody", Graziano, et al.
The Journal of Immunology, vol. 152, No. 11, 1994, pp. 5368-5374, "Efficient Tumor Cell Lysis Mediated by a Bispecific Single Chain Antibody Expressed in *Escherichia coli*", Gruber, et al.
Bioseparation, vol. 5, 1995, pp. 339-350, "Alternative modes of precipitation of Eudragit S-100: a potential ligand carrier for affinity precipitation of protein", Guoqiang, et al.
Journal of Molecular Recognition, vol. 9, 1996, pp. 356-359, XP-002538983, "Affinity Precipitation of Proteins", Gupta, et al.
Am Inst. of Chem Engineers Journal, Jul. 2003, vol. 49, No. 7, pp. 1687-1701, "Flocculation of Biological Cells: Experiment vs. Theory", Han, et al.
Analyst, vol. 129, 2004, pp. 421-427, "Capturing of acidic macromolecules from biological samples using a temperature-responsive polymer modified with poly-L-lysine", Hayashi, et al.
Journal of Chromatography B, vol. 790, Jun. 2003, pp. 79-90, "Protein purification by affinity precipitation", Hilbrig, et al.
The Proceedings of the National Academy of Sciences, USA, vol. 90, No. 14, Jul. 1993, pp. 6444-6448, "'Diabodies': Small bivalent and bispecific antibody fragments", Holliger, et al.
Journal of Molecular Biology, vol. 227, No. 2, Sep. 1992, pp. 381-388, "By-passing Immunisation: Human Antibodies from Synthetic Repertoires of Germline VH Gene Segments Rearranged in vitro", Hoogenboom, et al.
Molecular Immunology, vol. 28, No. 9, Sep. 1991, pp. 1027-1037, "Construction and expression of antibody-tumor necrosis factor fusion proteins", Hoogenboom, et al.
Biotechnology and Bioengineering, vol. 60, No. 5, Dec. 1998, pp. 568-579, "Preparation of a New Thermo-Responsive Adsorbent with Maltose as a Ligand and Its Application to Affinity Precipitation", Hoshino, et al.
Transplantation, vol. 58, No. 3, 1994, pp. 377-380, "Administration of an anti-CD11a monoclonal antibody in recipients of kidney transplantation. A pilot study", Hourmant, et al.
Biotechnology Techniques, vol. 4, No. 1, 1990, pp. 55-60, "The Flocculation of Bacteria Using Cationic Synthetic Flocculants and Chitosan", Hughes, et al.
Bioseparation, vol. 7, No. 4-5, 1999, pp. 207-220, "Polycomplexes—potential for bioseparation", Izumrudov, et al.
Proc. Natl. Acad. Sci. USA, vol. 90, Mar. 1993, pp. 2551-2555, "Analysis of homozygous mutant chimeric mice: Deletion of the immunoglobulin heavy-chain joining region blocks B-cell development and antibody production", Jakobovits, et al.

(56) References Cited

OTHER PUBLICATIONS

Nature, vol. 362, Mar. 1993, pp. 255-258, "Germ-line transmission and expression of a human-derived yeast artificial chromosome", Jakobovits, et al.

Nature, vol. 321, May 1986, pp. 522-525, "Replacing the complementarity-determining regions in a human antibody with those from a mouse", Jones, et al.

Cancer Research (Suppl.), vol. 55, Dec. 1995, pp. 5908s-5910s, "Radiolabeled Anti-CD33 Monoclonal Antibody M195 for Myeloid Leukemias", Jurcic, et al.

Cancer Research (Suppl.), vol. 55, Dec. 1995, pp. 5899s-5907s, "Treatment of Non-Hodgkin's Lymphoma with Radiolabeled Murine, Chimeric, or Humanized LL2, an Anti-CD22 Monoclonal Antibody", Juweid, et al.

Biotechnology and Bioengineering, vol. 40, No. 11, Dec. 1992, pp. 1381-1387, "Purification of Recombinant Protein A by Aqueous Two-Phase Extraction Integrated with Affinity Precipitation", Kamihira, et al.

Anal. Chem., vol. 69, No. 5, 1997, pp. 823-830, "Temperature-Responsive Liquid Chromatography. 2. Effects of Hydrophobic Groups in N-isopropylacrylamide Copolymer-modified Silica", Kanazawa, et al.

Journal of Chromatography A, vol. 1106, Feb. 2006, pp. 152-158, "Temperature-responsive stationary phase utilizing a polymer of proline derivative for hydrophobic interaction chromatography using an aqueous mobile phase", Kanazawa, et al.

Biochemical Engineering Journal, vol. 40, No. 3, 2008, pp. 512-519, "Flocculation enhanced microfiltration of Escherichia coli lysate", Karim, et al.

Journal of Membrane Science, vol. 182, No. 1-2, Feb. 2001, pp. 161-172, "Flocculation to enhance microfiltration", Kim, et al.

Flocculation in Biotechnology and Separation Systems, 1987, pp. 429-439, "Removal of Cell and Cell Debris by Electrostatic Adsorption of Positively Charged Polymeric Particles", Kim, et al.

Growth Factors, vol. 7, 1992, pp. 53-64, "The Vascular Endothelial Growth Factor Proteins: Identification of Biologically Relevant Regions by Neutralizing Monoclonal Antibodies", Kim, et al.

The Journal of Immunology, pp. 2453-2455, Reprinted with permission from Nature, vol. 256 (5517): 495-497 (1975), "Continuous cultures of fused cells secreting antibody of predefined specificity", Kohler, et al.

The Journal of Immunology, vol. 148, No. 5, 1992, pp. 1547-1553, "Formation of a bispecific antibody by the use of leucine zippers", Kostelny, et al.

The Journal of Immunology, vol. 133, No. 6, 1984, pp. 3001-3005, "A human hybrid myeloma for production of human monoclonal antibodies", Kozbor, et al.

Isolation and Purification of Proteins, 2003, edited by Rajni Hatti-Kaul, et al., pp. 237-275, "Precipitation of Proteins", Kumar, et al.

Biotechnology and Bioengineering, vol. 59, Issue 6, 1998, pp. 695-704, "Affinity Precipitation of Amylase Inhibitor from Wheat Meal by Metal Chelate Affinity Binding Using Cu(II)-Loaded Copolymers of 1-Vinylimidazole with N-Isopropylacrylamide", Kumar, et al.

Prog. Polym. Sci., vol. 32, 2007, pp. 1205-1237, "Smart polymers: Physical forms and bioengineering applications", Kumar, et al.

Biotechnology and Bioengineering, vol. 75, No. 5, Dec. 2001, pp. 570-580, "Type-Specific Separation of Animal Cells in Aqueous Two-Phase Systems Using Antibody Conjugates with Temperature-Sensitive Polymers", Kumar, et al.

Am Chem Society, ACS Symposium Series, vol. 362, Chapter 7, 1988, pp. 72-101, "Scale-Up of Bioseparations for Microbial and Biochemical Technology", Ladisch, et al.

Nature, vol. 227, No. 5259, Aug. 1970, pp. 680-685, "Cleavage of Structural Proteins during the Assembly of the Head of Bacteriophage T4", Laemmli.

Bioseparation, vol. 7, 1999, pp. 195-205, "Carboxymethyl cellulose as a new heterobifunctional ligand carrier for affinity precipitation of proteins", Lali, et al.

Journal of Biotechnology, vol. 49, No. 1-3, Aug. 1996, pp. 189-199, "Evaluation of affinity precipitation and a traditional affinity chromatographic precedure for purification of soybean lectin, from extracts of soya flour", Larsson, et al.

Journal of Pharmaceutical Sciences, vol. 100, No. 7, Jul. 2011, pp. 2551-2562, "Assessment of Net Charge and Protein-Protein Interactions of Different Monoclonal Antibodies", Lehermayr, et al.

AIChE Journal, vol. 55, No. 8, Aug. 2009, pp. 2070-2080, "Effect of Molecular Weight of Poly(N-isopropylacrylamide) Temperature-Sensitive Flocculants on Dewatering", Li, et al.

European Journal of Immunology, vol. 26, No. 1, Jan. 1996, pp. 1-9, "Antibody-targeted superantigen therapy induces tumor-infiltrating lymphocytes, excessive cytokine production, and apoptosis in human colon carcinoma", Litton, et al.

The Journal of Immunology, vol. 156, No. 4, 1996, pp. 1646-1653, "In Vivo Blockade of TNF-alpha by Intravenous Infusion of a Chimeric Monoclonal TNF-alpha Antibody in Patients with Rheumatoid Arthritis. Short Term Cellular and Molecular Effects", Lorenz, et al.

Journal of Chromatography B, vol. 878, No. 9-10, Mar. 2010, pp. 798-806, "Using precipitation by polyamines as an alternative to chromatographic separation in antibody purification processes", MA, et al.

Innovative Food Science and Emerging Technologies, 2007, pp. 1-11, "Novel chromatographic separation—The potential of smart polymers", Maharjan, et al.

Analytical Chemistry, vol. 75, No. 13, Jul. 2003, pp. 2943-2949, "A Smart Microfluidic Affinity Chromatography Matrix Composed of Poly(N-isopropylacrylamide)-Coated Beads", Malmstadt, et al.

Bioconjugate Chem., 2003, vol. 14, No. 3, pp. 575-580, "Affinity Thermoprecipitation and Recovery of Biotinylated Biomolecules via a Mutant Streptavidin-Smart Polymer Conjugate", Malmstadt, et al.

Journal of Molecular Biology, vol. 222 No. 3, Dec. 1991, pp. 581-597, "By-passing Immunization—Human Antibodies from V-gene Libraries Displayed on Phage", Marks, et al.

Bio/Technology, Nature Publishing Group, vol. 10, Jul. 1992, pp. 779-783, "By-Passing Immunization: Building High Affinity Human Antibodies by Chain Shuffling", Marks, et al.

Nature, vol. 348, Dec. 1990, pp. 552-554, "Phage antibodies: filamentous phage displaying antibody variable domains", McCafferty, et al.

Millipore Pure Science Laboratory Catalogue 1999/2000, Ultrafiltration Discs and Stirred Cells, p. 127, "Solvent-resistant Stirred Cells" and "High-Output Stirred Cells", 3 pages.

Nature, vol. 305, Oct. 1983, pp. 537-540, "Hybrid hybridomas and their use in immunohistochemistry", Milstein, et al.

Journal of Biochemical and Biophysical Methods, vol. 24, 1992, pp. 107-117, "Single-step purification of F(ab')sub.2 fragments of mouse monoclonal antibodies (immunoglobulins G1) by hydrophobic interaction high performance liquid chromatography using TSKgel Phenyl-5PW", Morimoto, et al.

Proc. Natl. Acad. Sci. USA, vol. 81, Nov. 1984, pp. 6851-6855, "Chimeric human antibody molecules: Mouse antigen-binding domains with human constant region domains", Morrison, et al.

American Inst. of Chem. Engineers, Biotechnology Progress, V 26, No. 5, (2010), pp. 1322-1331, "Monoclonal Antibody Purification Using Cationic Polyelectrolytes: An Alternative to Column Chromatography", Peram, et al.

Flocculation in Biotechnology and Separation Systems, 1987, pp. 457-466, "Flocculation of Cell Debris for Improved Separation by Centrifugation", Persson, et al.

The Journal of Immunology, vol. 151, No. 5, Sep. 1993, pp. 2623-2632, "Humanization of an Antibody Directed Against IgE", Presta, et al.

Current Opinion in Structural Biology, vol. 2, No. 4, Aug. 1992, pp. 593-596, "Antibody Engineering", Presta.

Cancer Research (Suppl.), vol. 55, Dec. 1995, pp. 5916s-5920s, "Radioimmunotherapy for Breast Cancer Using Escalating Fractionated Doses of 131-I-labeled Chimeric L6 Antibody with Peripheral Blood Progenitor Cell Transfusions", Richman, et al.

Nature, vol. 332, Mar. 1988, pp. 323-327, "Reshaping human antibodies for therapy", Riechmann, et al.

(56) References Cited

OTHER PUBLICATIONS

Final Rejection mailed Dec. 28, 2012 in co-pending U.S. Appl. No. 12/387,688.
Office Action-Restriction—mailed mailed Nov. 21, 2012 in co-pending U.S. Appl. No. 13/155,912.
International Search Report and Written opinion dated Jan. 29, 2010 in corresponding PCT application No. PCT/US09/67097, 8 pages.
International Preliminary Report on Patentability mailed Jun. 30, 2011 in corresponding PCT Patent Application No. PCT/US2009/067097, 7 pages.
Extended European Search Report mailed Nov. 17, 2009 in co-pending EP Patent Application No. 09161982.5, 6 pages.
International Search Report/Written Opinion mailed Nov. 12, 2009 in co-pending PCT Patent Application No. PCT/US2009/002787, 9 pages.
International Preliminary Report on Patentability issued Dec. 13, 2010 in co-pending PCT Patent Application No. PCT/US2009/002787, 6 pages.
Office Action dated Nov. 17, 2010 in co-pending U.S. Appl. No. 12/387,688.
Final Rejection dated Apr. 21, 2011 in co-pending U.S. Appl. No. 12/387,688.
Japanese Communication mailed Oct. 16, 2012 in corresponding Japanese patent application No. 2011-542238.
Journal of Biotechnology, vol. 128, No. 4, Mar. 2007, pp. 813-823, "The use of chitosan as a flocculant in mammalian cell culture dramatically improves clarification throughput without adversely impacting monoclonal antibody recovery", Riske, et al.
Biotechnol. Prog, vol. 24, No. 3, May/Jun. 2008, pp. 488-495, "Advances in Primary Recovery: Centrifugation and Membrane Technology", Roush, et al.
Anal. Chem., vol. 71, No. 20, Oct. 1999, pp. 4506-4512, "Concentration of Hydrophobic Organic Compounds by Polymer-Mediated Extraction", Saitoh, et al.
Kona, No. 20, 2002, pp. 246-250, "Flocculation Mechanism of Suspended Particles Using the Hydrophilic/Hydrophobic Transition of a Thermosensitive Polymer", Sakohara, et al.
Advanced Drug Delivery Reviews, vol. 58, No. 15, 2006, pp. 1655-1670, "Thermo- and pH-responsive polymers in drug delivery", Schmaljohann.
The Journal of Physical Chemistry B, vol. 111, No. 29, 2007, pp. 8649-8654, "Cationic Flocculants Carrying Hydrophobic Functionalities: Applications for Solid/Liquid Separation", Schwarz, et al.
Biotechnology and Bioengineering, vol. 34, No. 3, 1989, pp. 387-393, "Purification of Wheat Germ Agglutinin Using Affinity Flocculation with Chitosan and a Subsequent Centrifugation or Flotation Step", Senstad, et al.
Macromolecules, American Chemical Society, vol. 24, No. 15, 1991, pp. 4255-4263, "Self-organization of Poly(allylamine)s Containing Hydrophobic Groups and Its Effect on the Interaction with Small Molecules. 1. Static Fluorometry", Seo, et al.
J. Exp. Med., vol. 175, 1992, pp. 217-225, "Development of Humanized Bispecific Antibodies Reactive with Cytotoxic Lymphocytes and Tumor Cells Overexpressing the HER2 Protooncogene", Shalaby, et al.
Journal of Biotechnology, vol. 49, 1996, pp. 173-178, "Flocculation of cell, cell debris and soluble protein with methacryloyloxyethyl trimethylammonium chloride-acrylonitrile copolymer", Shan, et al.
Cancer Research (Suppl.), vol. 55, Dec. 1995, pp. 5935s-5945s, "Evaluation of a Complementarity-Determining Region-Grafted (Humanized) Anti-Carcinoembryonic Antigen Monoclonal Antibody in Preclinical and Clinical Studies", Sharkey, et al.
The Journal of Immunology, vol. 151, No. 4, 1993, pp. 2296-2308, "A Humanized CD18 Antibody Can Block Function Without Cell Destruction", Sims, et al.
Chest, vol. 103, No. 3, Mar. 1993, pp. 932-943, "Immunologic Therapy for ARDS, Septic Shock, and Multiple-Organ Failure", St. John, et al.
Cell, vol. 66, No. 6, 1991, pp. 1133-1144, "The B Lymphocyte Adhesion Molecule CD22 Interacts with Leukocyte Common Antigen CD45RO on T Cells and a2-6 Sialyltransferase, CD75, on B Cells", Stamenkovic, et al.
The Affinity Precipitation for the Isolation of Biomolecules, No. 3862, Aug. 2007, pp. 1-130, 146 pages, Stocker-Majd, et al, submitted in two parts.
Transplant International, vol. 4, No. 1, 1991, pp. 3-7, "Anti-LFA1 monoclonal antibody (25.3) for treatment of steroid-resistant grade III-IV acute graft-versus-host disease", Stoppa, et al.
Journal of Chromatography A, vol. 1114, 2006, pp. 239-249, "Temperature sensitive dopamine-imprinted (N,N-methylene-bis-acrylamide cross-linked) polymer and its potential application to the selective extraction of adrenergic drugs from urine", Suedee, et al.
Analytical Sciences, vol. 3, No. 6, Dec. 1987, pp. 479-488, "Ion-Association Reagents, A Review", Toei.
The EMBO Journal, vol. 10, No. 12, 1991, pp. 3655-3659, "Bispecific single chain molecules (Janusins) target cytotoxic lymphocytes on HIV infected cells", Traunecker, et al.
The Journal of Immunology, vol. 147, No. 1, Jul. 1991, pp. 60-69, "Trispecific F(ab')3 derivatives that use cooperative signaling via the TCR/CD3 complex and CD2 to activate and redirect resting cytotoxic T cells", Tutt, et al.
Flocculation in Biotechnology and Separation Systems, 1987, pp. 351-368, "Aspects of Bioflocculation: An Overview", Unz.
Nature Biotechnology, vol. 14, 1996, pp. 309-314, "Human Antibodies with Sub-nanomolar Affinities Isolated from a Large Non-immunized Phage Display Library", Vaughan, et al.
Science, vol. 239, Mar. 1988, pp. 1534-1536, "Reshaping Human Antibodies: Grafting an Antilysozyme Activity", Verhoeyen, et al.
Nucleic Acids Research, vol. 21, No. 9, 1993, pp. 2265-2266, "Combinatorial infection and in vivo recombination: a strategy for making large phage antibody repertoires", Waterhouse, et al.
Biotechnology and Bioengineering, vol. 108, No. 1, Jan. 2011, pp. 50-58, "Effects of Solution Environment on Mammalian Cell Fermentation Broth Properties: Enhanced Impurity Removal and Clarification Performance", Westoby, et al.
Biotechnology and Bioengineering, vol. 86, No. 6, 2004, pp. 612-621, "Clearance of Minute Virus of Mice by Flocculation and Microfiltration", Wickramasinghe, et al.
Desalination, vol. 147, No. 1-3, 2002, pp. 25-30, "Enhanced microfiltration of yeast by flocculation", Wickramasinghe, et al.
Separation Science and Technology, vol. 37, No. 1, pp. 217-228, 2002, "Selective Precipitation of Water-Soluble Proteins Using Designed Polyelectrolyte", Yu, et al.
Protein Engineering, vol. 8, No. 10, 1995, pp. 1057-1062, "Engineering linear F(ab')2 fragments for efficient production in *Escherichia coli* and enhanced antiproliferative activity", Zapata, et al.
Nucleic Acids Research, vol. 31, No. 13, 2003, pp. 3406-3415, "Mfold web server for nucleic acid folding and hybridization prediction", Zuker.
International Search Report mailed Mar. 31, 2008 in co-pending PCT application No. PCT/US2007/26040.
International Search Report dated Apr. 24, 2008 in co-pending PCT application No. PCT/US2007/26090.
International Search Report dated Aug. 27, 2009 in co-pending PCT application No. PCT/US2008/013736.
International Search Report dated Feb. 18, 2010 in co-pending PCT application No. PCT/US2009/006363.
International Search Report/Written Opinion dated Dec. 6, 2011 in co-pending PCT application No. PCT/US2011/039595.
International Search Report dated Oct. 31, 2011 in co-pending PCT application No. PCT/US2011/036648.
Office Action mailed Jun. 11, 2010 in co-pending U.S. Appl. No. 12/004,319.
Final Rejection mailed Apr. 13, 2011 in co-pending U.S. Appl. No. 12/004,319.
Office Action mailed Oct. 3, 2011 in co-pending U.S. Appl. No. 12/004,319.
Notice of Allowance mailed May 9, 2012 in co-pending U.S. Appl. No. 12/004,319.

(56) References Cited

OTHER PUBLICATIONS

Notice of Allowance mailed Aug. 15, 2012 in co-pending U.S. Appl. No. 12/004,319.
Office Action mailed Jun. 21, 2011 in co-pending U.S. Appl. No. 12/316,708.
Office Action mailed Feb. 29, 2012 in co-pending U.S. Appl. No. 12/316,708.
Office Action-Restriction—mailed Feb. 7, 2012 in co-pending U.S. Appl. No. 12/448,004.
Office Action mailed Jul. 26, 2012 in co-pending U.S. Appl. No. 12/448,004.
Office Action-Restriction—mailed Apr. 27, 2012 in co-pending U.S. Appl. No. 12/592,744.
Office Action Feb. 21, 2012 in co-pending U.S. Appl. No. 12/387,688.
Final Rejection mailed Sep. 25, 2012 in co-pending U.S. Appl. No. 12/316,708.
Notice of Allowance mailed Oct. 1, 2012 in co-pending U.S. Appl. No. 12/004,319.
Office Action-Restriction—mailed Jul. 17, 2012 in corresponding U.S. Appl. No. 12/633,141.
French Search Report dated Jun. 2, 2009 in co-pending French patent application No. FA 713810/FR 0854844.
Office Action mailed Feb. 26, 2009 in co-pending U.S. Appl. No. 11/805,539.
Office Action mailed May 26, 2009 in co-pending U.S. Appl. No. 11/805,539.
Office Action mailed Jul. 30, 2009 in co-pending U.S. Appl. No. 11/805,539.
Final Rejection mailed Dec. 29, 2009 in co-pending U.S. Appl. No. 11/805,539.
Final Rejection mailed Apr. 20, 2010 in co-pending U.S. Appl. No. 11/805,539.
Final Rejection mailed Aug. 27, 2010 in co-pending U.S. Appl. No. 11/805,539.
Final Rejection mailed Jan. 7, 2011 in co-pending U.S. Appl. No. 11/805,539.
Office Action mailed Apr. 21, 2011 in co-pending U.S. Appl. No. 11/805,539.
Final Rejection mailed Oct. 18, 2011 in co-pending U.S. Appl. No. 11/805,539.
Advisory Action mailed Nov. 25, 2011 in co-pending U.S. Appl. No. 11/805,539.
Examiner's Answer to Appeal Brief mailed Jul. 3, 2012 in co-pending U.S. Appl. No. 11/805,539.
Office Action mailed Nov. 1, 2011 in co-pending U.S. Appl. No. 12/383,131.
Final Rejection mailed Apr. 13, 2012 in co-pending U.S. Appl. No. 12/383,131.
Office Action mailed Jun. 11, 2013 in co-pending U.S. Appl. No. 12/383,131.
Final Rejection mailed Oct. 24, 2013 in co-pending U.S. Appl. No. 12/383,131.
Office Action mailed Feb. 4, 2014 in co-pending U.S. Appl. No. 12/383,131.
Office Action mailed Feb. 27, 2014 in co-pending U.S. Appl. No. 12/387,688.
Office Action mailed Apr. 3, 2014 in corresponding U.S. Appl. No. 12/633,141.
Office Action-Restiction—mailed Sep. 30, 2014 in co-pending U.S. Appl. No. 13/732,613.
Japanese communication, with English translation, dispatched Sep. 2, 2014 in corresponding Japanese patent application No. 2013-083213.
Journal of the Chemical Society of Japan, No. 8, Aug. 1991, pp. 1115-1126 (English Abstract Submitted), "Structure and Hydrolysis Activity of Poly(alylamine)s having Hydrophobic Groups", Seo, et al.
Final Rejection mailed Jun. 23, 2014 in co-pending U.S. Appl. No. 12/383,131.

Final Rejection mailed Aug. 8, 2014 in co-pending U.S. Appl. No. 13/747,495.
Notice of Allowance mailed Aug. 4, 2014 in co-pending U.S. Appl. No. 13/955,024.
Office Action mailed Jul. 29, 2014 in co-pending U.S. Appl. No. 12/387,688.
Final Rejection mailed Aug. 14, 2014 in corresponding U.S. Appl. No. 12/633,141.
Notice of Allowance dated Jun. 4, 2015 in co-pending U.S. Appl. No. 12/383,131.
Final Rejection dated Jul. 27, 2015 in corresponding U.S. Appl. No. 12/633,141.
Office Action dated Mar. 16, 2015 in co-pending U.S. Appl. No. 13/732,613.
Office Action dated Mar. 2, 2015 in corresponding U.S. Appl. No. 12/633,141.
Notice of Allowance dated Feb. 20, 2015 in co-pending U.S. Appl. No. 12/387,688.
Office Action dated Dec. 19, 2014 in co-pending U.S. Appl. No. 12/383,131.
Final rejection dated Oct. 20, 2015 in co-pending U.S. Appl. No. 13/732,613.
Office action dated Sep. 17, 2015 in co-pending U.S. Appl. No. 13/747,495.
Notice of Allowance dated Sep. 4, 2015 in co-pending U.S. Appl. No. 13/955,024.
Notice of Allowance dated Nov. 6, 2015 in co-pending U.S. Appl. No. 13/955,024.
Notice of Allowance dated May 11, 2016 in co-pending U.S. Appl. No. 11/805,539.
Notice of Allowance dated Jun. 9, 2016 in co-pending U.S. Appl. No. 11/805,539.
Notice of Allowance dated Feb. 10, 2016 in co-pending U.S. Appl. No. 11/805,539.
Notice of Allowance dated Mar. 2, 2016 in co-pending U.S. Appl. No. 13/747,495.
Final rejection dated Feb. 25, 2016 in co-pending U.S. Appl. No. 12/633,141.
Majd, Gisela S., "The affinity precipitation for the isolation of biomolecules" Thèse EPFL, No. 3862, pp. 1-130, Aug. 2007.
International Preliminary Report on Patentability dated Jun. 24, 2009 in co-pending PCT application No. PCT/US2007/026040.
International Preliminary Report on Patentability dated Jun. 24, 2009 in co-pending PCT application No. PCT/US2007/026090.
International Preliminary Report on Patentability dated Jun. 22, 2010 in co-pending PCT application No. PCT/US2008/013736.
Japanese communication, with English translation, dated Jul. 19, 2016 in co-pending Japanese patent application No. 2015-215483.
Notice of Allowance dated Oct. 3, 2016 in co-pending U.S. Appl. No. 13/955,024.
Office action dated Sep. 21, 2016 in co-pending U.S. Appl. No. 12/633,141.
Final rejection dated Jan. 27, 2017 in co-pending U.S. Appl. No. 12/633,141.
Final rejection dated May 2, 2017 in co-pending U.S. Appl. No. 13/732,613.
Hemstrom et al., "Hydrophilic Interaction Chromatography," Journal of Separation Science, vol. 29, Iss. 12, pp. 1784-1821, Aug. 2006.
Nisnevitch et al., "The Solid Phase in Affinity Chromatography: Strategies for Antibody Attachment," Journal of Biochemical and Biophysical Methods, vol. 49, pp. 467-480, Oct 30, 2001.
Wang, "Ion Exchange in Purification," Separation Processes in Biotechnology, pp. 359-400, 1990.
Advisory action dated Apr. 27, 2017 in co-pending U.S. Appl. No. 12/633,141.
Chiang et al., "Application of Superparamagnetic Nanoparticles in Purification of Plasmid DNA from Bacterial Cells," Journal of Chromatography B, vol. 822, pp. 54-60, Aug. 5, 2005.
Office action dated Oct. 11, 2016 in co-pending U.S. Appl. No. 13/732,613.
Office action dated Oct. 5, 2016 in co-pending U.S. Appl. No. 14/940,864.

(56) References Cited

OTHER PUBLICATIONS

Office action dated Sep. 12, 2017 in co-pending U.S. Appl. No. 13/955,024.

* cited by examiner

STIRRED TANK REACTOR AND METHOD

This application is a divisional of U.S. patent application Ser. No. 12/633,141 filed Dec. 8, 2009, which claims priority of Provisional Application Ser. No. 61/201,865 filed Dec. 16, 2008, the disclosures of which are hereby incorporated by reference.

FIELD OF THE INVENTION

The present invention relates to stirred tank containers, and related methods.

BACKGROUND OF THE INVENTION

The general process for the manufacture of biomolecules, such as proteins, particularly recombinant proteins, typically involves two main steps: (1) the expression of the protein in a host cell, followed by (2) the purification of the protein. The first step involves growing the desired host cell in a bioreactor to effect the expression of the protein. Some examples of cell lines used for this purpose include Chinese hamster ovary (CHO) cells, myeloma (NSO) bacterial cells such as e-coli and insect cells. Once the protein is expressed at the desired levels, the protein is removed from the host cell and harvested. Suspended particulates, such as cells, cell fragments, lipids and other insoluble matter are typically removed from the protein-containing fluid by filtration or centrifugation, resulting in a clarified fluid containing the protein of interest in solution as well as other soluble impurities.

The second step involves the purification of the harvested protein to remove impurities which are inherent to the process. Examples of impurities include host cell proteins (HCP, proteins other than the desired or targeted protein), nucleic acids, endotoxins, viruses, protein variants and protein aggregates. This purification typically involves several chromatography steps, which can include affinity chromatography, ion exchange, hydrophobic interaction, etc. on solid matrices such as porous agarose, polymeric or glass or by membrane based adsorbers.

One example of a chromatography process train for the purification of proteins involves protein-A affinity, followed by cation exchange, followed by anion exchange. The protein-A column captures the protein of interest or target protein by an affinity mechanism while the bulk of the impurities pass through the column to be discarded. The protein then is recovered by elution from the column. Since most of the proteins of interest have isoelectric points (PI) in the basic range (8-9) and therefore being positively charged under normal processing conditions (pH below the PI of the protein), they are bound to the cation exchange resin in the second column. Other positively charged impurities are also bound to this resin. The protein of interest is then recovered by elution from this column under conditions (pH, salt concentration) in which the protein elutes while the impurities remain bound to the resin. The anion exchange column is typically operated in a flow through mode, such that any negatively charged impurities are bound to the resin while the positively charged protein of interest is recovered in the flow through stream. This process results in a highly purified and concentrated protein solution.

Other alternative methods for purifying proteins have been investigated in recent years. One such method involves a flocculation technique. In this technique, a soluble polyelectrolyte is added to an unclarified cell culture broth to capture the suspended particulates and a portion of the soluble impurities thereby forming a flocculant, which is subsequently removed from the protein solution by filtration or centrifugation.

Alternatively, a soluble polyelectrolyte is added to clarified cell culture broth to capture the biomolecules of interest, thereby forming a flocculant, which is allowed to settle and can be subsequently isolated from the rest of the solution. The flocculant is typically washed to remove loosely adhering impurities. Afterwards, an increase in the solution's ionic strength brings about the dissociation of the target protein from the polyelectrolyte, subsequently resulting in the resolubilization of the polyelectrolyte into the protein-containing solution.

In co-pending application U.S. Ser. No. 12/004,314 filed Dec. 20, 2007, the disclosure of which is hereby incorporated by reference, a polymer, soluble under certain conditions, such as temperature, pH, salt, light or combinations thereof, is used to bind impurities while in its soluble state and is then precipitated out upon a change in condition (pH or temperature, etc.) removing the impurities with it. The biomolecule of interest is then further treated using traditional chromatography or membrane adsorbers and the like.

All of the protein purification technologies discussed above share a common theme, namely, to first remove suspended particulates in a first distinct step and then in a second step separate the biomolecules of interest from soluble impurities which are inherent to the process.

In situ product recovery with derivatized magnetic particles is one example of a protein purification technique where the biomolecules of interest can be purified directly from an un-clarified cell culture broth. In this technique, a polymer shell encapsulating a magnetic bead is functionalized with an affinity ligand that seeks out and binds the target protein. A magnetic field is then applied to collect the bead-protein complexes, leaving behind the soluble impurities and insoluble particulates.

The main drawback of this technique is that it requires appreciable capital investments in design, construction and validation of high-gradient magnetic separators. Also, the technique does not lend itself to disposable applications, which are poised to become the norm for protein purification in the Bioprocess industry.

In co-pending application filed Dec. 16, 2008 under Ser. No. 12/316,708, entitled "Purification of Proteins" by Moya, Wilson, et al., the disclosure of which is hereby incorporated by reference, there is disclosed a polymer such as a soluble polymer capable of substantially irreversibly binding to insoluble particulates and a subset of soluble impurities and also capable of reversibly binding to one or more desired biomolecules in an unclarified biological material containing stream and the methods of using such a material to purify one or more desired biomolecules from such a stream without the need for prior clarification. More specifically, this co-pending application discloses a stimuli responsive polymer such as a selectively soluble polymer capable of selectively and reversibly binding to one or more desired biomolecules in an unclarified biological material containing stream and the methods of using such a polymer to purify one or more desired biomolecules from such a complex mixture of materials including the biomolecule(s) of interest and various impurities such as other proteins (host cell proteins), DNA, virus, whole cells, cellular debris and the like without the need for prior clarification of the stream.

The polymer is soluble under a certain set of process conditions such as one or more of pH, salt concentration, temperature, light, or electrical field, and is able to interact and complex with insoluble impurities (cells, debris, etc.)

and a fraction of the soluble impurities, and is rendered insoluble and precipitates out of solution upon a change in conditions (temperature, salt concentration, light, electrical field, or pH), e.g. a stimuli responsive polymer. Only when precipitated out of solution, the polymer is capable of reversibly binding to one or more desired biomolecules within the stream (protein, polypeptide, etc.) in an unclarified cell broth. The precipitate can then be removed from the stream, such as by being filtered out from the remainder of the stream and the desired biomolecule is recovered such as by selective elution from the precipitate.

The removal of the precipitate, however, can be problematic, as it is typically in the form a large mass of sludge.

It would be desirable to provide an apparatus and method for the efficient purification of samples, particularly those containing biomolecules, preferably within a single, integral, apparatus that reduces or eliminates one or more process steps that can result in contamination or material loss.

SUMMARY OF THE INVENTION

The problems of the prior art have been overcome by the embodiments disclosed herein, which include a container or housing for sample preparation or processing, such as biomass culturing or processing, and optionally sample purification. In certain embodiments, the container or housing is a mixer. In certain embodiments, the container or housing is a reactor. In certain embodiments, the reactor is a bioreactor, which can be disposable or reusable, that includes a stirred cell device that can simulate a tangential flow filter to reduce or eliminate clogging that can be caused by the solids generated. In certain embodiments, the solids comprise a precipitate or floc, such as one that includes a polymer that binds the biomolecule(s) of interest, and impurities such as cells and cell components. In certain embodiments, the stirred cell component includes one or more membranes for purification, such as during recovery (e.g., by elution) of the biomolecule(s) of interest. In certain embodiments, the biomolecules are proteins, polypeptides or antibodies. In certain embodiments, the container has two compartments. In certain embodiments the container has two compartments each of which has a membrane with it. In certain embodiments, the container has two compartments, the first having a membrane, the second being in fluid communication with a filter device downstream of the second compartment outlet.

In its method aspects, embodiments disclosed herein include purification and isolation of biomolecules of interest derived from cell culture fluids. In certain embodiments, the methods include carrying out sample preparation or processing in a container or housing, such as culturing a biomass; generating solids such as by precipitating or flocculating a biomolecule of interest from the cultured broth; preventing the solids from settling in the container by agitation; and purification, such as by binding and eluting the biomolecule of interest and filtering the same. In certain embodiments, the sample processing involves expressing a protein of interest. In certain embodiments, the solids comprise a precipitate that includes a polymer bound to the protein of interest, and the purification involves binding and elution and one or more filtration steps. In certain embodiments, the solids comprise a precipitate that includes a polyelectrolyte bound to the protein of interest, and the purification involves binding and elution and one or more filtration steps. In certain embodiments, the polymer is bound to the impurities (cells, cell debris, etc.) and the biomolecule remains in the supernatant. The precipitation step may replace conventional chromatographic separations, may be used as a direct capture step to isolate the protein of interest from the cell culture broth, or may simply be an intermediate purification step. In certain embodiments, affinity or ion exchange beads or beads having any ligand or functionality capable of purifying the biomolecule may be used instead of a polymer to bind a biomolecule of interest. In certain embodiments, the one or more filtration steps are carried out in situ in the same apparatus as the sample processing. In certain embodiments, the eluted protein is subjected to further purification, such as by affinity and/or ion exchange chromatography.

DETAILED DESCRIPTION

Suitable containers or housings useful here in useful herein are not particularly limited. For purposes of illustration, reactors, and in particular, bioreactors, will be discussed in detail, which include disposable as well as reusable bioreactors. For example, solvent-resistance bioreactors having a borosilicate glass cylinder and PTFE components, such as those commercially available from Millipore Corporation, can be used. Similarly, disposable bioreactors that utilize bags, or that are formed of semi-rigid or rigid molded plastic, can be used. Such disposable bioreactors are generally pre-sterilized. Means for agitation within the bioreactor is also not particularly limited, and includes impeller-based agitation, magnetic stirrers, as well as wave-induced agitation and agitation induced by gas bubbles. Agitation is important in preventing solids from settling and plugging the one or more membranes used for purification.

The following description is in reference to a bioreactor. Those skilled in the art will appreciate that it is for illustrative purposes only, and that the embodiments disclosed herein are applicable to any container containing a liquid sample having, or ultimately forming, a sample having a relatively high solids content.

Figure 1:
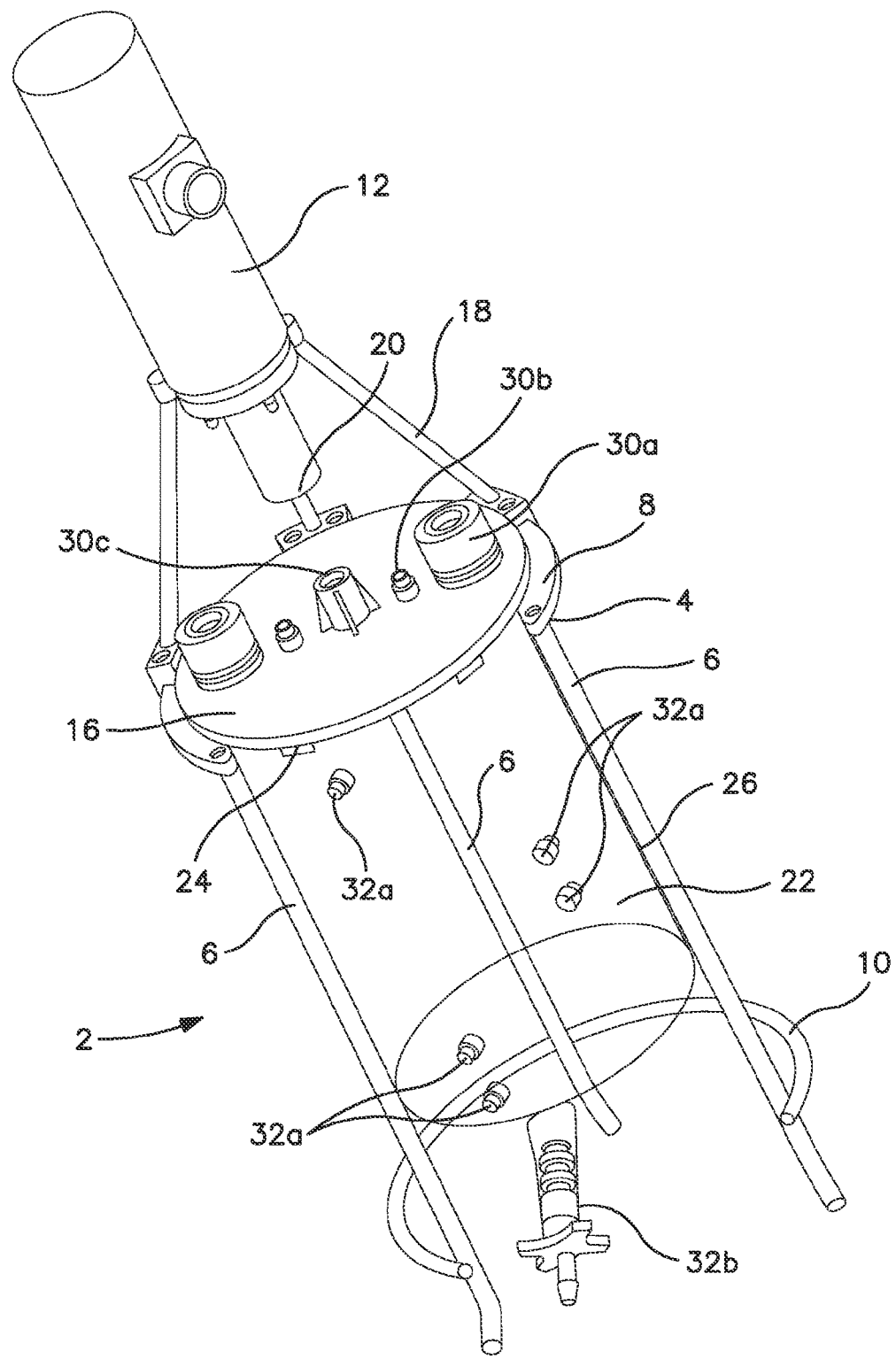
FIG. 1 is a perspective view of a bioreactor in accordance with certain embodiments.
Figure 2:
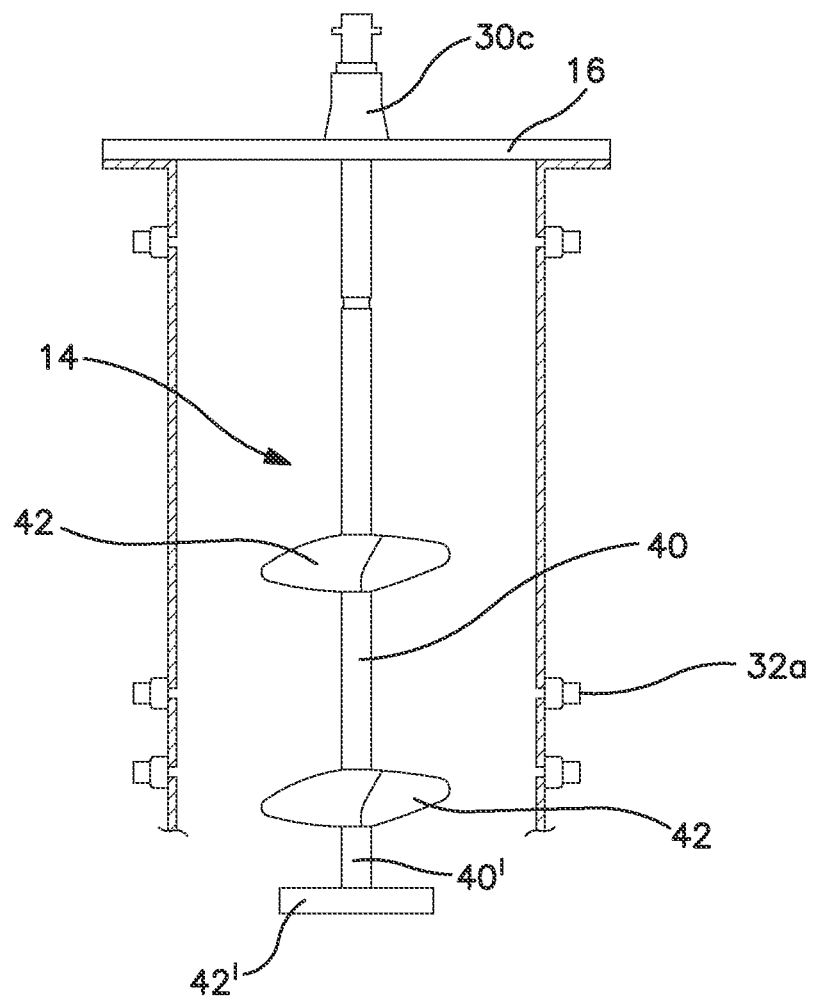
FIG. 2 is a cross-sectional view of a portion of the bioreactor of FIG. 1.

Turning now to FIGS. 1 and 2, bioreactor 2 is shown held in a stand 4, which is comprised of several legs 6 (in this embodiment 3 legs although one continuous leg or 2 large legs or more than 3 legs can also be used) and a support rim 8. As shown the legs 6 may have an optional support piece 10 at or near the bottom to keep the legs 6 from spreading when the bioreactor 2 is filled and in the stand 4.

Depending upon the type of circulation or agitation system used, the stand 4 may also support the drive mechanism 12 (as shown) for the circulation mechanism, which typically is a stirrer or paddle assembly 14. In this particular embodiment, the drive mechanism 12 is a motor and is mounted to the top of the centered above the top 16 of the bioreactor 2 by several arms 18 (although 3 are shown alternative numbers may be used). Other features such as mounting blocks (not shown) and the like may be formed on the top 16 or support rim 8 to support the drive mechanism 12. As shown, the drive mechanism 12 has a shaft 20 that can be attached to the stirrer as explained later herein. Other stands can be used in lieu of the design described above and will work equally well.

The bioreactor body 22 (only partially shown in FIG. 1) has an interior space into which the fluids, cells, probes and other devices of the bioreactor are at least partially contained. The body 22 is sealably attached to the top 16. This may be by a mechanical seal such as a rubber gasket and clips 24 (as shown) or by a clamp, such as a band clamp or Ladish or TriClover clamp, mated threads on the top 16 and body 22 and the like. Alternatively, they may be sealed by adhesives or heat sealing of the top 16 to the body 22 or formed together in one piece such as in a rotomolding apparatus.

The body 22 has one or more sidewalls 26 that extend downwardly from the top 16. As shown, there is one sidewall 26 of a circular or cylindrical design. Alternatively, there can be 3, 4, or more sidewalls if desired (not shown).

Preferably, the body 22 is made of a single piece of molded plastic or glass. Alternatively it may be made of two or more pieces of plastic or glass that are sealed together such as by heat, glue, or gaskets (not shown). Suitable polymers which can be used to form the top and body include but are not limited to polycarbonates, polyesters, nylons, PTFE resins and other fluoropolymers, acrylic and methacrylic resins and copolymers, polysulphones, polyethersulphones, polyarylsulphones, polystyrenes, polyetherimides, nylons, polyesters, polyethylene terephthalates (PET), polyvinyl chlorides, chlorinated polyvinyl chlorides, ABS and its alloys and blends, polyolefins, preferably polyethylenes such as linear low density polyethylene, low density polyethylene, high density polyethylene, and ultrahigh molecular weight polyethylene and copolymers thereof, polypropylene and copolymers thereof and metallocene generated polyolefins. Preferred polymers are polyolefins, in particular polyethylenes and their copolymers; polystyrenes; and polycarbonates. The top and body may be made of the same polymer or different polymers as desired. In reusable embodiments, the body can be made of glass, acrylic, or other materials not deleterious to the process. The body 22 also can be a disposable plastic bag, as is known in the art.

Also formed in the bioreactor 2 of this embodiment are one or more ports 30 (in this embodiment there are three types 30a-c (for a total of 5 ports) formed in the top 16 and one or more ports 32 in the body 22 (in this embodiment there are at least two different types 32a-b for a total of seven ports overall). The top 16 and body 22 may have multiple ports of similar and/or of different styles to provide one with the number of ports, of the desired type, in the desired locations throughout the bioreactor 2. These ports 30, 32 or at least a portion of them are formed as part of the top 16 and/or body 22. They may be formed with threads that mate to sealable covers such as closed caps, gasketed caps with a throughbore within the gasket, or various Luer fittings. Alternatively, one or more of the ports can be made in the plastic top 16 and/or body 22 by drilling or burning a hole and then mounting (such as by heat bonding or adhesives) a port in place through or around the hole. Many different port styles and sizes can be accommodated.

Ports 30a may be used for liquid or gas entrance or exit or for probes such as pH probes, thermometers or thermocouples or the like. Ports 30b may be used for similar purposes. Port 30c is for the stirrer shaft described in further detail herein. Alternatively, if the bioreactor is an airlift design and doesn't use a stirrer rod, the port 30c may be used to house the airline to the sparger at or near the bottom of the body or for any other desired purpose. Ports 32a may be used for sampling of the liquid or for probes such as pH, temperature, dissolved oxygen, lactose level, etc. as are common on such bioreactors. Ports 32a while shown as being formed on the sidewall 26 may also be formed in the bottom if desired as shown in FIG. 2. Port 32b is valved port which can be used to supply gas to the body 22 and/or as a drain or outlet from the body. It may serve both functions by attaching a 3 position valve or Y-shaped tube with valves such as pinch valves on each arm of the Y to control flow (not shown). One suitable system for the valve of port 32b is a LYNX® connector available from Millipore Corporation of Billerica, Mass. and as shown in US Patent Publication No. 2005/0016620.

Preferably, one or more ports 32 of the body are formed in a location that is below the normal liquid/gas interface level of the bioreactor.

If desired, one or more of the ports 32a or b in FIG. 1 may be used to provide gases to the body's interior. A plastic frit such as a POREX® porous material, a microporous membrane or ceramic stone or sintered metal filter may be attached to the inside of the port within the body to provide the sized gas bubbles desired. Alternatively, a port 30a in the top 16 may be used to hold a tube that extends down into the body to provide the gas supply. Again it may use a frit or ceramic stone or sintered metal filter or a membrane to provide the desired bubble size. Alternatively, gases can be provided to the interior of the body through the porous filter/membrane 110 within the stirred cell assembly and the supply of gas can be provided through port 32b.

FIG. 2 shows a bioreactor 2 with top 16 and body 22 sealed to each other and a suitable stirring mechanism 14 in place. The stirring mechanism shown is formed of a shaft 40 and one or more paddles, circular disk, impellers, vanes or the like 42. The shaft 40 extends through port 30c and is connected to the shaft 20 of the drive mechanism 12 (not shown). Preferably one or more o-rings in the port 30c allow for movement of the shaft 40 without compromising the integrity of the seal within the body 22. Alternatively, the "agitation" to avoid plugging can be effected by ultrasonic waves or vibration directed at the membrane or filter surface to prevent the solids from collecting on the surface. Another method to prevent plugging the filter/membrane is to cause the solids to float to the top of the liquid phase by introducing gas bubbles which adhere to the solids.

Figure 7:
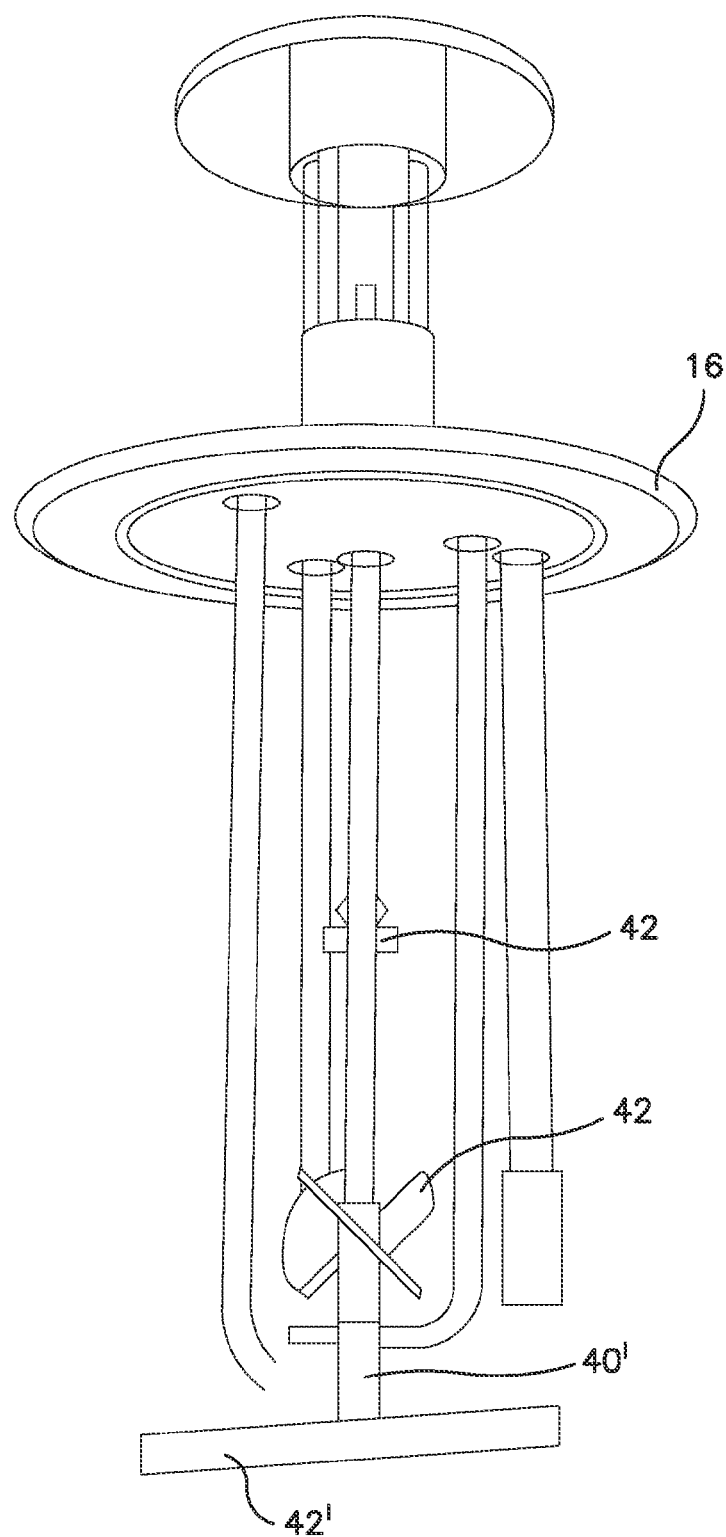
FIG. 7 is a perspective view of an agitator in accordance with certain embodiments.

In accordance with certain embodiments, the bioreactor is a cylindrical tube, and is removably and sealingly affixed to a base in order to provide a stirred cell assembly. For example, in the embodiment shown, shaft 40 is extended below paddle 42 via a short shaft portion 40', and an additional paddle or the like 42' is added (FIG. 7). The paddle 42' is preferably positioned just above the membrane 110 (discussed below) in the base in order to avoid contact with the membrane which could damage it. So positioned, it agitates the fluid just above the membrane and prevents solids (e.g., affinity beads, precipitate or floc) from settling on the membrane, which tend to clog or plug the pores of the membrane. Preferably the paddle is sufficiently wide such that it substantially corresponds to the width of the effective diameter of the membrane, or is slightly smaller than such width, in order to provide uniform fluid agitation over the effective filtration area of the membrane. In certain embodiments, the paddle 42' can be constructed of a suitable material, such as rubber or a sponge-like material, so that contact with the surface of the membrane during agitation does not damage the membrane, and is acceptable, in order to further ensure that solids do not settle on the membrane surface. Those skilled in the art will appreciate that suitable means other than a paddle, such as a circular disk or wave agitation, to sufficiently agitate the fluid in the interior space of the body 22, are within the scope of the embodiments disclosed herein.

Figure 3:
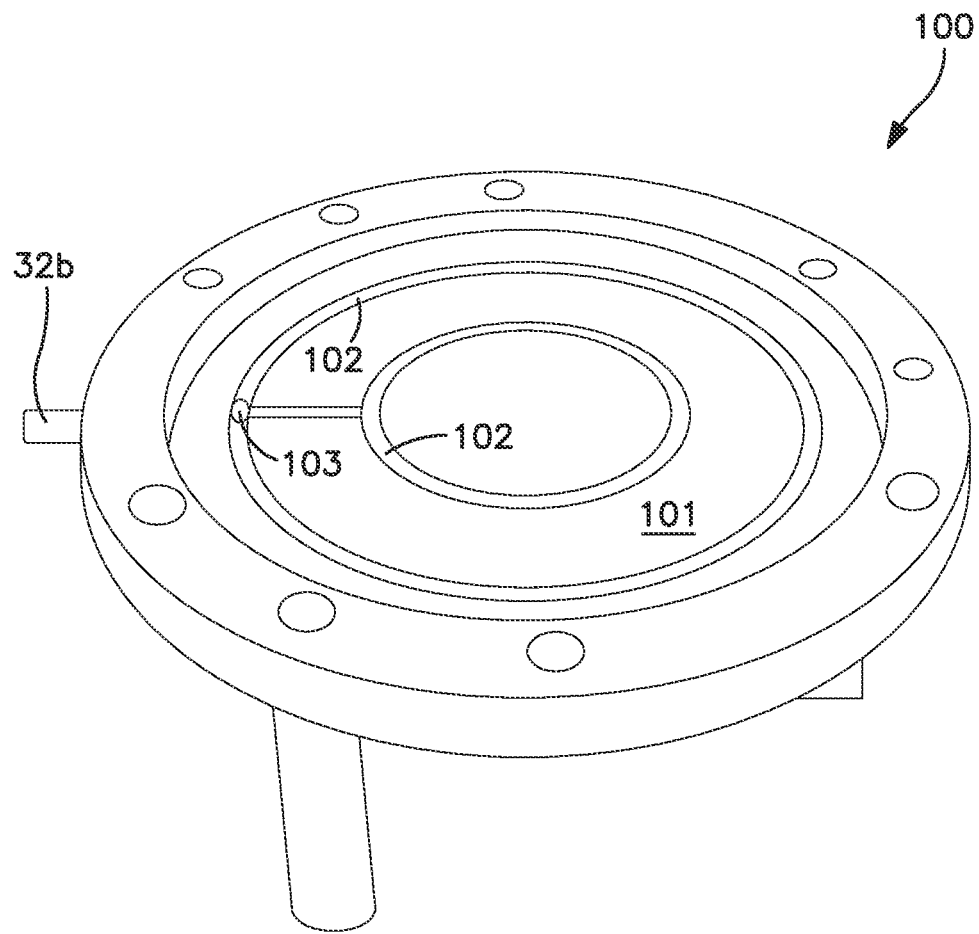
FIG. 3 is a perspective view of a bioreactor base in accordance with certain embodiments.

Turning to FIG. 3, a bioreactor base 100 is shown, which includes a supporting surface 101 formed with grooves 102 or the like for the flow of fluid. The configuration of grooves 102 is not particularly limited, although the preferred configuration is concentric circles as illustrated. The grooves 102 are in fluid communication with an aperture 103, which in turn is in fluid communication with port 32*b*, for draining fluid from the base 100.

Figure 4:
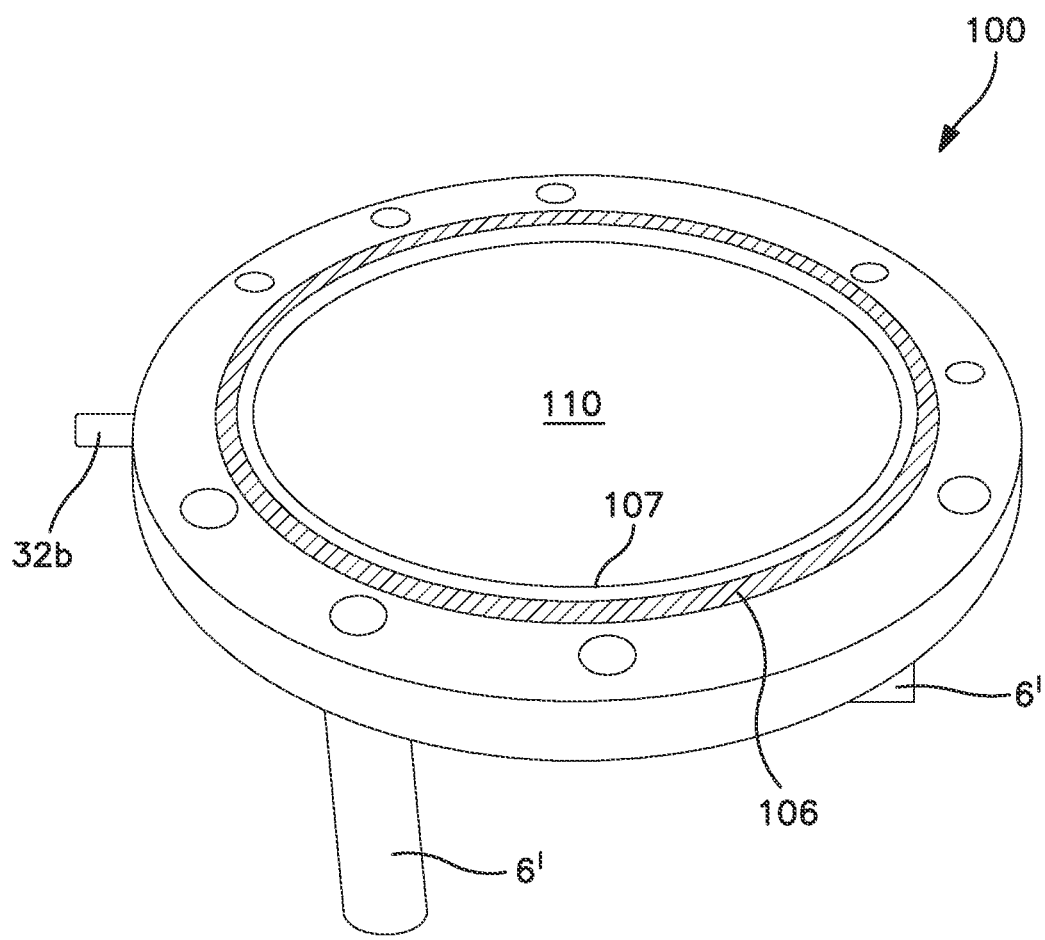
FIG. 4 is a perspective view of the base of FIG. 3, including a membrane sealed thereon.

The surface 101 of the base 100 supports one or more membranes 110 (FIG. 4). Preferably one of the one or more membranes is a relatively coarse filter or membrane, particularly when the solids content of the broth is high, such as about 20-35% solids by volume. Use of a coarse filter or membrane as an initial filtration step helps protect and prolong the service life of subsequent downstream filtration through tighter, generally more expensive membranes, such as a 0.2 micron sterilizing grade membrane (discussed in greater detail below). Suitable membranes include, but are not limited to, polymers such as but not limited to olefins such as polyethylene including ultrahigh molecular weight polyethylene, polypropylene, EVA copolymers and alpha olefins, metallocene olefinic polymers, PFA, MFA, PTFE, polycarbonates, vinyl copolymers such as PVC, polyamides such as nylon, polyesters, cellulose, cellulose acetate, regenerated cellulose, cellulose composites, polysulfone, polyethersulfone, polyarylsulfone, polyphenylsulfone, polyacrylonitrile, polyvinylidene fluoride (PVDF), and blends thereof. The membrane selected depends upon the application, desired filtration characteristics, particle type and size to be filtered and the flow desired. Preferred membrane based filters include DURAPORE® PVDF membranes available from Millipore Corporation of Billerica Mass., MILLIPORE EXPRESS® and MILLIPORE EXPRESS® PLUS or SH PES membranes available from Millipore Corporation of Billerica Mass. Prefilters, depth filters and the like can also be used in these embodiments such as Polygard® prefilters (Polygard CE prefilters) and depth filters (Polygard CR depth filters) available from Millipore Corporation of Billerica Mass.

Depending on the mixture, polymer and the nature of biomolecule, the filter may be hydrophilic or hydrophobic. Preferred filters are hydrophilic and are low in protein binding.

The filter, be it membrane or otherwise, may be symmetric in pore size throughout its depth such as DURAPORE® PVDF membranes available from Millipore Corporation of Billerica Mass., or it may be asymmetric in pore size through its thickness as with MILLIPORE EXPRESS® and MILLIPORE EXPRESS® PLUS or SH PES membranes available from Millipore Corporation of Billerica Mass. It may contain a prefilter layer if desired, either as a separate upstream layer or as an integral upstream portion of the membrane itself.

Depending on the size of the particles generated, there may be instances in which the membrane is an ultrafiltration membrane. For example, in cases in which the particle size is small compared to the pore size of a microporous membrane, then a membrane with smaller pores (in the UF range) would be more appropriate to avoid plugging. Suitable ultrafiltration membranes include regenerated cellulose and polyethersulfone membranes, including those with a pore size larger than 0.2 microns, e.g., generally those with pore sizes of 0.45, 0.65, 1.0, 2.0 microns or larger. Optionally a porous support (not shown) can be placed between the surface 101 of the base and the membrane(s) 110. The membrane(s) (and support if present) are sealed against the base such as with an O-ring 106, which in turn can be held in place by a support ring 107, such as an acrylic ring. Where more than one membrane 110 is used, they can be assembled in a stacked relationship. Where more than one membrane is used, each membrane need not be of the same performance characteristics (e.g, pore size, flux, capacity, surface chemistry, etc). For example, the upper membrane against the paddle 42' may be of a larger pore size than the lower membrane(s) and/or it may be of a different material than the lower membrane(s).

Figure 5:
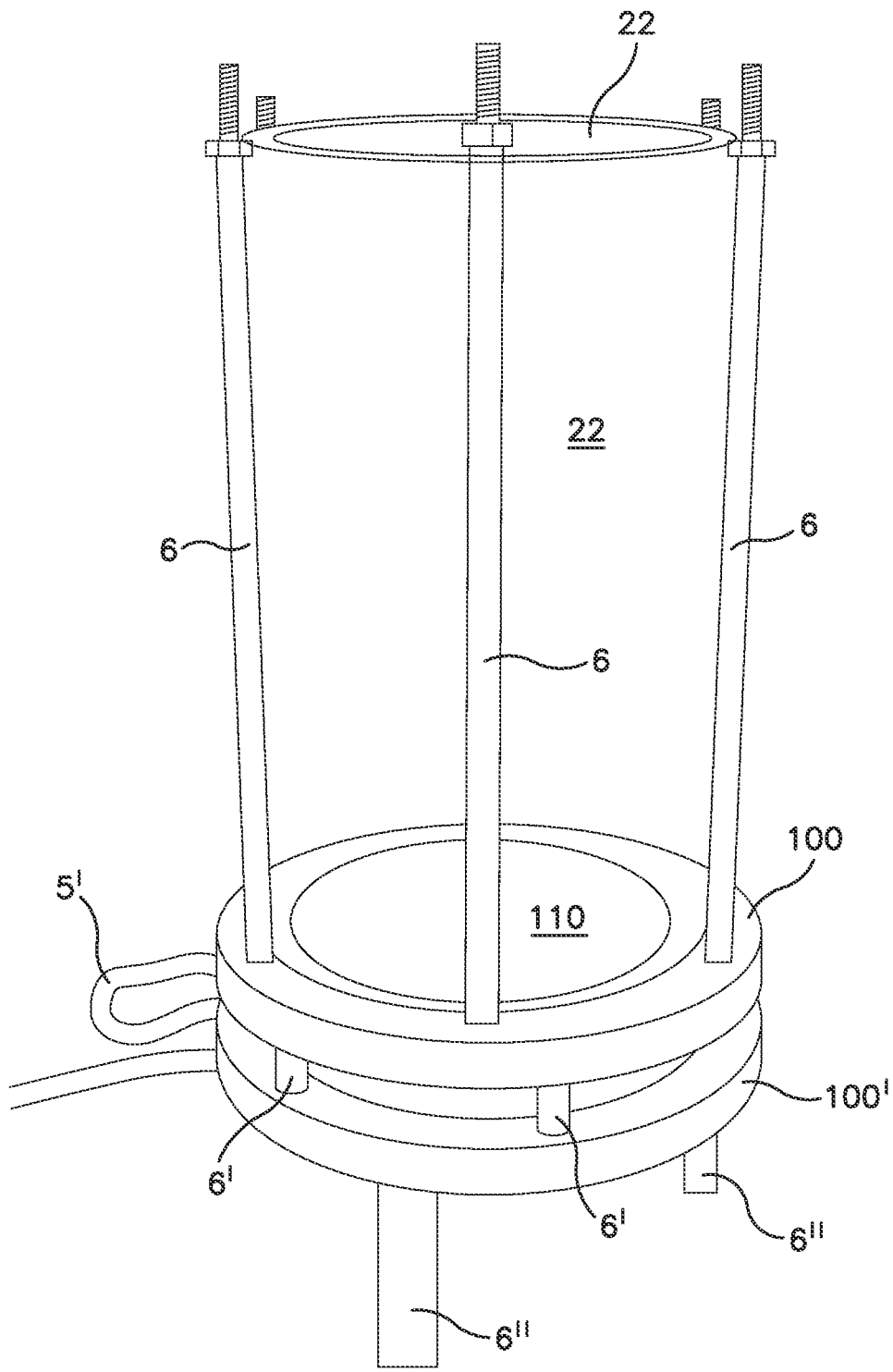
FIG. 5 is a perspective view of a bioreactor assembly, including a housing, a bioreactor base, and a filtration base.

The bioreactor body 22, such as a cylindrical tube, is placed in sealing relationship with the base 100, as shown in FIG. 5. A plurality of legs 6' can be provided, which extend downwardly from the base 100 to support the same.

Figure 6:
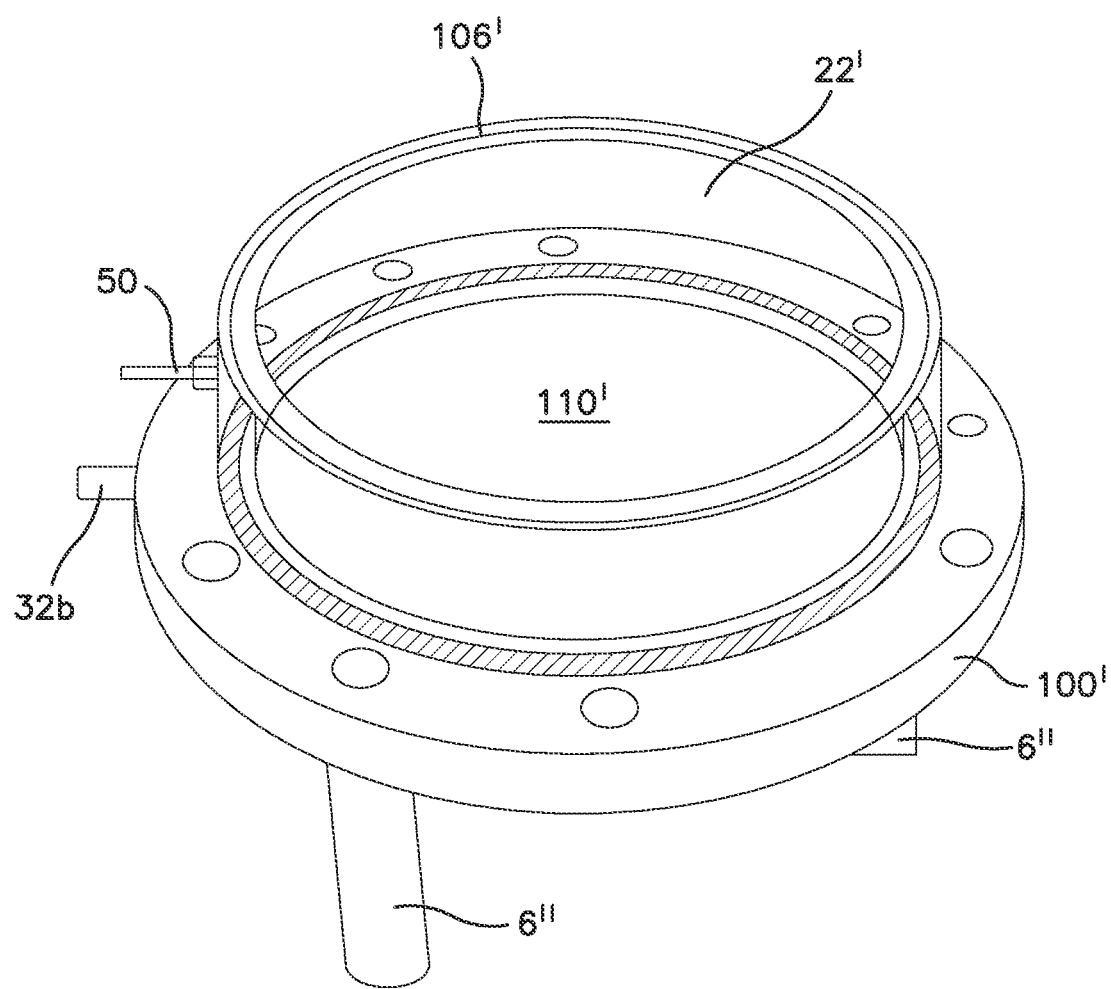
FIG. 6 is a perspective view of a filtration base in accordance with certain embodiments.

In certain embodiments, where additional purification is desired, a further filter base can be added to the assembly, as shown in FIGS. 5 and 6. Thus, a base 100', similar to base 100, is provided, again with a supporting surface having suitable grooves, and one or more membranes sealingly supported thereon, such as with a suitable O-ring and support ring. For example, a sterilizing membrane, such as a 0.2 micron membrane, can be used (optionally along with a suitable porous support). Sealed to the filter base 100' is a housing 22', which provides a cavity or interior space between the bioreactor base 100 and the filter base 100'. The housing 22' can be a cylindrical tube, preferably having the same diameter as the bioreactor housing 22, and made of the same material. It should have a height sufficient to accommodate at least a portion of the volume of fluid to be purified that is received directly from the bioreactor. The top edge of the housing 22' preferably protrudes radially inwardly, and preferably includes an O-ring 106' so that the housing 22' and base 100 can be affixed in sealing relation. A plurality of legs 6" can be provided, extending downwardly from the base 100' to support the assembly. Although it is preferred that the filter base 100' be integral to the bioreactor assembly to form a one-piece reactor assembly for sample processing and direct purification, in certain embodiments this subsequent purification step could be carried out with a filter that is physically separate from (although optionally in fluid communication with) the bioreactor body 22.

The housing 22' includes an inlet port 50 that can be placed in fluid communication with the outlet 32*b* of the base 100, such as with suitable tubing 51 (FIG. 5). The filter base 100' includes an outlet port 32*b*' in fluid communication with the drain (not shown) in the base, for directing the biomolecule of interest to a suitable point of use, such as a further purification step (e.g, a chromatography process train).

An alternative embodiment is to have the outlet of the second housing 22' in fluid communication with the outlet 32 of the base 100 but to have the second housing contain no filter or membrane. Instead the outlet port 32' is in fluid communication via a tube or other conduit (not shown) with a self contained filter device (not shown) such as a Millex® filter or an Optiscale® or Opticap® filter that then sterile filters the biomolecule of interest. The outlet of this filter device is then connected to a suitable point of use, such as a further purification step (e.g., a chromatography process train).

Suitable valving and sensing equipment can be associated with one or more of the various inlets and outlets to detect or measure and control flow or any other characteristic, such as the presence of the biomolecule or the presence of impurities, as appropriate or desired. For example, during the cell culture phase, the outlet 32b of the base 100 is closed so that the fluid remains in the body 22 when the gas is applied through port 32a or 30a.

In certain embodiments where a polymer is added to a cell culture broth to selectively and releasably bind a biomolecule of interest, suitable polymers include poly(N-vinyl caprolactam), poly(N-acryloylpiperidine), poly(N-vinylisobutyramide), poly(N-substituted acrylamide) including [poly(N-isopropylacrylamide), poly(N,N'-diethylacrylamide), and poly(N-acryloyl-N-alkylpiperazine)], Hydroxyalkylcellulose, copolymers of acrylic acid and methacrylic acid, polymers and copolymers of 2 or 4-vinylpyridine and chitosan with either a ligand or functional group attached to it.

Suitable biomolecules of interest include proteins and antibodies. Suitable antibodies include antibody selected from the group consisting of a recombinant antibody, a recombinant monoclonal antibody, a polyclonal antibody, a humanized antibody and an antibody fragment.

In operation, the sterile device is placed within the stand and the various connections for air, liquid, probes, sampling, etc. are attached to the device at the appropriate ports. The device is filled with media to a desired level forming a liquid/air interface somewhere below where the top 16 is attached to the body 22 to leave a head space of gas as is common in such devices. At least one port 32 is below the level of the interface.

The media is then seeded with the organism to be grown, be it plant, animal cell (CHO or NSO cells for instance) virus, yeast, mold or bacteria (such as E. coli) and the liquid is circulated or agitated and air/gases and liquids moved into or out of the device in a manner to effectively grow the culture inside.

A polymer soluble under a certain set of process conditions is added, and is rendered insoluble and precipitates out of solution upon a change in conditions (e.g., temperature, salt concentration, light, electrical field, or pH). Alternatively, affinity or ion exchange beads or beads having any ligand or functionality capable of purifying the biomolecule can be added to bind to the biomolecule of interest or to the soluble impurities. Agitation is continued to inhibit the solids from settling, and the solid, which in this embodiment includes the precipitate that contains the polymer, impurities such as cells and cell debris, host cell proteins, DNA and the like and the desired biomolecule, can be washed one or more times (such as with a suitable buffer) to ensure that any impurities in the liquid or entrapped in or on the polymer have been removed. The wash step(s) can be carried out by filtration through the one or more membranes in the base 100, with supernatant being sent to waste via port 32b.

The biomolecule of interest then can be recovered, such as by selective elution of the target biomolecule from the precipitate (or beads) such as by altering the ionic strength and/or pH conditions of the solution while the impurities, including soluble and insoluble material, remain complexed with the precipitated polymer. Recovery is carried out preferably along with a sterilizing filtration step, by causing the filtration base 100' to be in fluid communication with the base 100, such as by connecting the outlet of the base 100 to the inlet 50 of the body 22'. Accordingly, permeate from the outlet of the base 100 enters the body 22', wets the membrane 110', and filtration through the membrane 110' proceeds. The purified biomolecule of interest is then recovered in the elution pool via the outlet port 32b' of base 100'. The precipitated polymer-impurity complex (or the affinity beads) may be discarded. The driving force for filtration may be pressure or vacuum.

What is claimed is:

1. A method for purifying a biomolecule selected from the group consisting of proteins and antibodies, from a mixture containing impurities selected from the group consisting of cells, cell debris, host cell proteins and DNA, comprising:
   a. providing an assembly comprising providing a first container having an interior space, a first base sealingly affixed to said first container and supporting at least one membrane sealed to said first base for filtering said mixture; an outlet in said base, a second container in fluid communication with the outlet of said first base, and a second base sealingly affixed to said second container, said second base comprising a second membrane and a supporting surface comprising grooves for fluid flow;
   b. providing the mixture at a set of conditions,
   c. adding one or more polymers, soluble in said mixture under the set of conditions and capable of reversibly and selectively binding to the biomolecule, said one or more polymers selected from the group consisting of poly(N-vinyl caprolactam), poly(N-acryloylpiperidine), poly(N-vinylisobutyramide), poly(N-isopropylacrylamide), poly(N,N'-diethylacrylamide), poly(N-acryloyl-N-alkylpiperazine), hydroxyalkylcellulose, copolymers of acrylic acid and methacrylic acid, and polymers and copolymers of 2 or 4-vinylpyridine and chitosan with either a ligand or functional group attached to it,
   d. mixing the one or more solubilized polymers throughout the mixture;
   e. precipitating the one or more polymers and bound biomolecule out of solution by changing the set of conditions in the mixture;
   f. washing said precipitate by contacting said precipitate with a wash solution and filtering the supernatant through said first membrane, and
   g. recovering the bound biomolecule from the polymer and filtering the biomolecule through said second membrane.

* * * * *